US010335325B2

(12) United States Patent
Sheldon et al.

(10) Patent No.: US 10,335,325 B2
(45) Date of Patent: Jul. 2, 2019

(54) ERGONOMIC DISPOSABLE ABSORBENT GARMENT

(71) Applicant: Advanced Absorbent Technologies, LLC, Downingtown, PA (US)

(72) Inventors: Donald A. Sheldon, Downingtown, PA (US); Joseph Howard, Glenmoore, PA (US); William Terenzoni, Jamison, PA (US)

(73) Assignee: Advanced Absorbent Technologies, LLC, Downingtown, PA (US)

(*) Notice: Subject to any disclaimer, the term of this patent is extended or adjusted under 35 U.S.C. 154(b) by 0 days.

(21) Appl. No.: 15/709,946

(22) Filed: Sep. 20, 2017

(65) Prior Publication Data
US 2018/0008488 A1    Jan. 11, 2018

Related U.S. Application Data

(63) Continuation-in-part of application No. 15/625,132, filed on Jun. 16, 2017, which is a continuation of (Continued)

(51) Int. Cl.
*A61F 13/49*    (2006.01)
*A61F 13/532*   (2006.01)
(Continued)

(52) U.S. Cl.
CPC .... *A61F 13/5376* (2013.01); *A61F 13/49017* (2013.01); *A61F 13/534* (2013.01);
(Continued)

(58) Field of Classification Search
CPC .......... A61F 13/49011; A61F 13/49017; A61F 13/49019; A61F 13/4902; A61F 13/4906;
(Continued)

(56) References Cited

U.S. PATENT DOCUMENTS 4,381,783 A   5/1983   Elias
4,695,278 A   9/1987   Lawson
(Continued)

FOREIGN PATENT DOCUMENTS

EP   0401189 A1   12/1990
EP   0724418 B1    8/1996
(Continued)

OTHER PUBLICATIONS

Communication Relating to the Results of the Partial International Search for PCT/US2014/025963 dated Aug. 14, 2014.
(Continued)

*Primary Examiner* — Catharine L Anderson
(74) *Attorney, Agent, or Firm* — Caesar Rivise, PC

(57) ABSTRACT

A disposable undergarment is disclosed. The undergarment includes a chassis and an absorbent core assembly. The chassis includes a front section, a crotch section and a rear section. The absorbent core is located in the crotch section, with portions of it extending into the front and rear sections. A large plurality of closely spaced elastic threads extends across the full width of the undergarment in the front and rear sections. A large plurality of closely spaced elastic threads extends across the full width of the undergarment in portions of the crotch section adjacent the front and rear sections. The elastic threads are broken in the areas of the core assembly. The core assembly includes a first section of a slow acting but high absorbency SAP in pockets thereof and an underlying second section of a fast acting by lower absorbency SAP in pockets thereof.

29 Claims, 5 Drawing Sheets

Related U.S. Application Data application No. 15/042,859, filed on Feb. 12, 2016, now Pat. No. 9,693,911, which is a continuation-in-part of application No. 14/204,616, filed on Mar. 11, 2014, now Pat. No. 9,707,135.

(60) Provisional application No. 61/792,004, filed on Mar. 15, 2013.

(51) Int. Cl.
    *A61F 13/537*     (2006.01)
    *A61G 17/04*     (2006.01)
    *A61F 13/534*     (2006.01)
    *A61F 13/53*     (2006.01)

(52) U.S. Cl.
    CPC .......... *A61F 13/5323* (2013.01); *A61G 17/04* (2013.01); *A61G 17/042* (2016.11); *A61G 17/047* (2016.11); *A61F 2013/49025* (2013.01); *A61F 2013/49036* (2013.01); *A61F 2013/530562* (2013.01); *A61F 2013/530715* (2013.01); *A61F 2013/530722* (2013.01); *A61F 2013/530737* (2013.01); *A61F 2013/530868* (2013.01)

(58) Field of Classification Search
    CPC ............ A61F 13/5323; A61F 13/53752; A61F 13/5376; A61F 2013/15463; A61F 2013/49025; A61F 2013/49026; A61F 2013/49028; A61F 2013/49033; A61F 2013/49036; A61F 2013/530481; A61F 2013/530547; A61F 2013/530562; A61F 2013/5307; A61F 2013/530708; A61F 2013/530715; A61F 2013/530722; A61F 2013/530729; A61F 2013/530737
    See application file for complete search history.

(56) References Cited

U.S. PATENT DOCUMENTS

| | | | |
|---|---|---|---|
| 4,743,346 A | 5/1988 | Graham et al. | |
| 4,846,823 A | 7/1989 | Enloe | |
| 4,994,053 A | 2/1991 | Lang | |
| 5,055,103 A | 10/1991 | Nomura et al. | |
| 5,163,932 A | 11/1992 | Nomura et al. | |
| 5,415,644 A | 5/1995 | Enloe | |
| D362,120 S | 9/1995 | Suskind et al. | |
| 5,447,508 A | 9/1995 | Numano et al. | |
| 5,599,338 A | 2/1997 | Enloe | |
| 5,762,641 A | 6/1998 | Bewick-Sonntag et al. | |
| 5,788,684 A | 8/1998 | Abuto et al. | |
| 5,938,650 A | 8/1999 | Baer et al. | |
| 5,977,014 A | 11/1999 | Plischke et al. | |
| 6,171,682 B1 | 1/2001 | Raidel et al. | |
| 6,258,196 B1 | 7/2001 | Suzuki et al. | |
| 6,626,879 B1 | 9/2003 | Ashton et al. | |
| 6,689,115 B1 | 2/2004 | Popp et al. | |
| 7,112,189 B2 | 9/2006 | Otsubo et al. | |
| 7,765,614 B2 | 8/2010 | Takino et al. | |
| 7,887,522 B2 | 2/2011 | Roe et al. | |
| 7,981,100 B2 * | 7/2011 | Takahashi | A61F 13/49019 604/385.22 |
| 8,257,331 B2 * | 9/2012 | Fujioka | A61F 13/15593 604/385.01 |
| 8,257,334 B2 | 9/2012 | Buell et al. | |
| 8,622,984 B2 | 1/2014 | Rajala et al. | |
| 8,646,506 B2 | 2/2014 | Ukegawa et al. | |
| 2003/0109840 A1 | 6/2003 | Dodge, II et al. | |
| 2003/0135177 A1 | 7/2003 | Baker | |
| 2003/0150551 A1 | 8/2003 | Baker | |
| 2004/0133180 A1 * | 7/2004 | Mori | A61F 13/15593 604/385.25 |
| 2005/0075617 A1 | 4/2005 | Vartiainen | |
| 2006/0069367 A1 | 3/2006 | Waksmundzki et al. | |
| 2006/0153984 A1 | 7/2006 | Suzuki et al. | |
| 2006/0184146 A1 | 8/2006 | Suzuki | |
| 2007/0032766 A1 | 2/2007 | Liu et al. | |
| 2008/0312628 A1 | 12/2008 | Hundorf et al. | |
| 2010/0069872 A1 | 3/2010 | Lindstrom | |
| 2011/0166540 A1 | 7/2011 | Yang | |
| 2013/0102982 A1 | 4/2013 | Nakano et al. | |
| 2013/0284362 A1 | 10/2013 | Tsujimoto et al. | |
| 2014/0276503 A1 | 9/2014 | Sheldon et al. | |
| 2016/0158075 A1 | 6/2016 | Sheldon et al. | |
| 2017/0112683 A1 * | 4/2017 | Fukasawa | A61F 13/49011 |

FOREIGN PATENT DOCUMENTS

| | | |
|---|---|---|
| EP | 1257240 B1 | 11/2002 |
| EP | 2444046 A1 | 4/2012 |
| EP | 2679210 A1 | 1/2014 |
| WO | 2011162652 A1 | 12/2011 |

OTHER PUBLICATIONS

International Search Report for PCT/US2014/025983 dated Dec. 3, 2014.
International Search Report for PCT/US2016/021310 dated Oct. 20, 2016.
International Search Report for PCT/US2018/022111 dated Jul. 20, 2018.

* cited by examiner

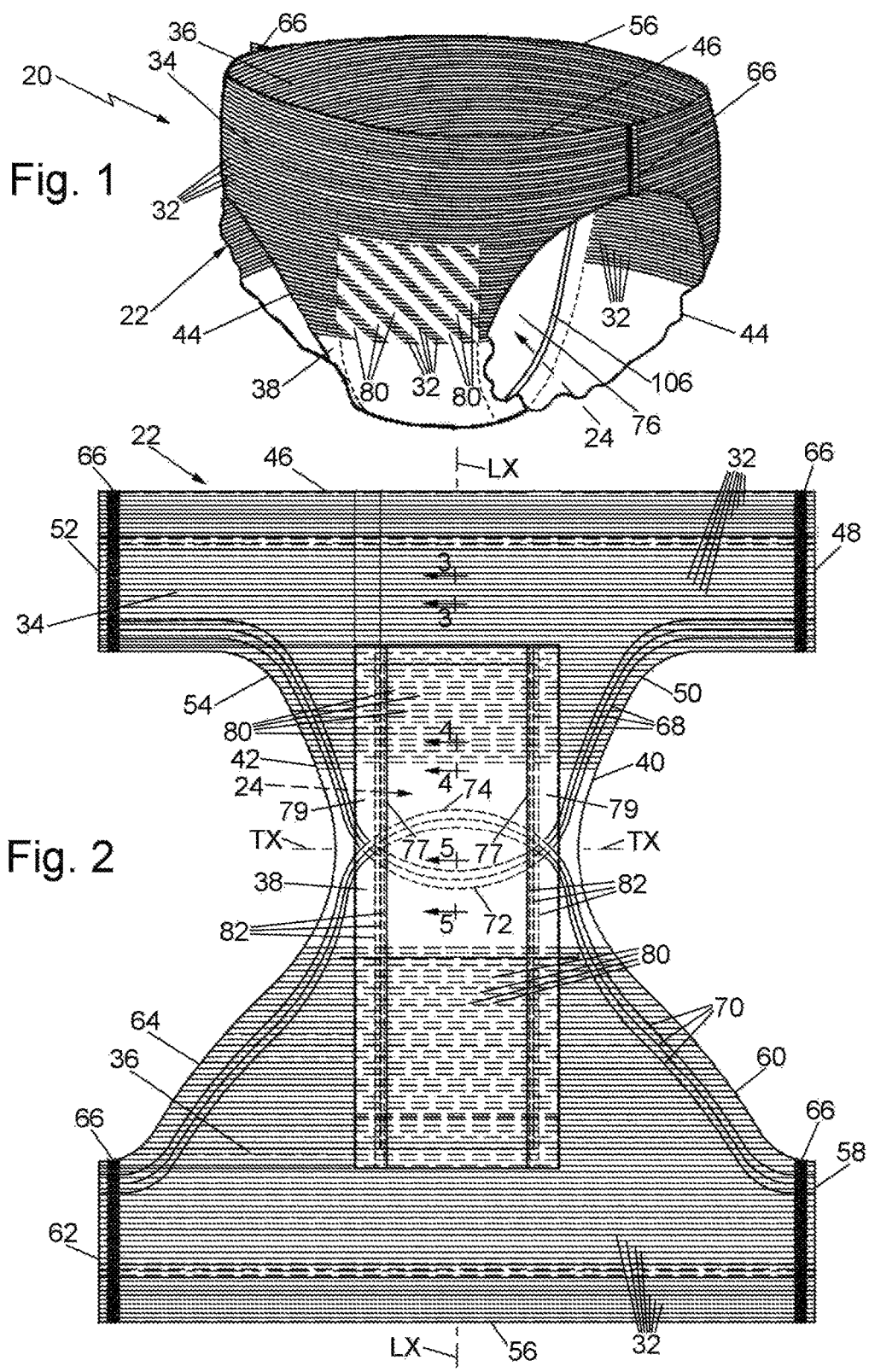

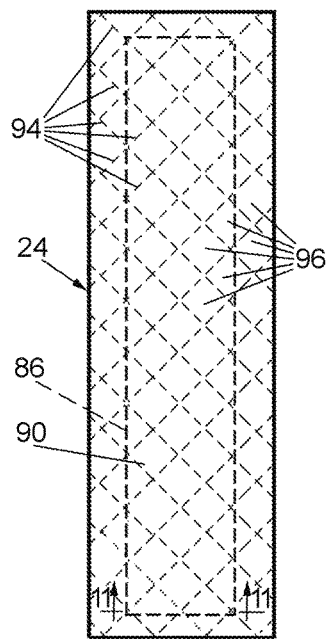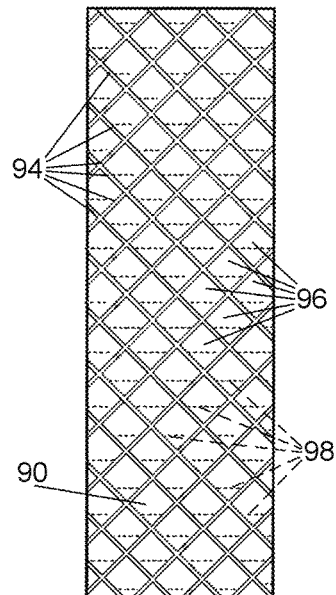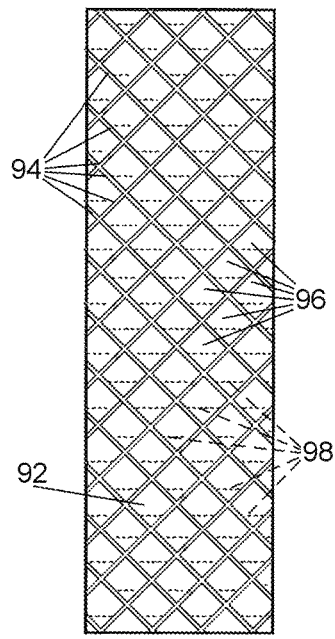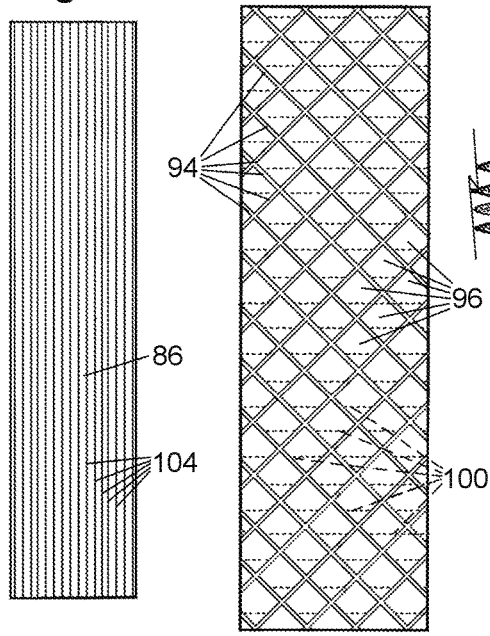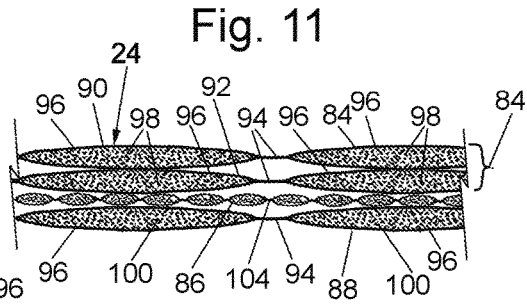

ERGONOMIC DISPOSABLE ABSORBENT GARMENT

CROSS-REFERENCE TO RELATED APPLICATIONS

This application constitutes a Continuation-In-Part of our prior application, Ser. No. 15/625,132, filed on Jun. 16, 2017, entitled Absorbent Products And Absorbent Core For Use In Same, which in turn is a continuation of our prior application Ser. No. 15/042,859, filed on Feb. 12, 2016, entitled Core Assembly For Absorbing Liquids, now U.S. Pat. No. 9,693,911, which in turn is a Continuation-In-Part of our prior application Ser. No. 14/204,616, filed on Mar. 11, 2014, entitled Disposable Absorbent Article, now U.S. Pat. No. 9,707,135, which in turn claims priority from U.S. Provisional Application Ser. No. 61/792,004, filed Mar. 15, 2013, entitled Disposable Absorbent Article, all of which applications are assigned to the same assignee as this invention, and whose disclosures are incorporated by reference herein.

FIELD OF THE INVENTION

This invention relates generally to disposable absorbent products and more particularly to disposable absorbent garments for adults.

BACKGROUND OF THE INVENTION

Various disposable undergarments are commercially available today from various manufacturers for use by adults having problems with incontinence. Examples of such products are men's and women's briefs sold under the trademark Depend® by Kimberly-Clark Corporation. The Depend® products utilize a chassis mounting an absorbent core in the crotch region of the chassis. The chassis itself comprises a colored nonwoven with approximately fifty seven transversely extending strands of white spandex elastic threads laminated between layers of a nonwoven spunbond fabric to impart elasticity to hold the undergarment close to the body of the wearer. The spacing between the elastic fibers is relatively large, e.g., 6-7 mm, so that the chassis exhibits a somewhat puckered appearance.

Other manufacturers provide similar types of undergarments making use of chassis for holding an absorbent core, wherein the chassis includes a plurality of transversely extending elastic threads or filaments to render the undergarment close-fitting in the interest of concealability and wearer comfort. For example, Proctor & Gamble offers incontinence underwear under the trademark Always®. That product also makes use of a chassis comprising approximately fifty seven transversely extending and relatively widely spaced strands of white spandex elastic threads sandwiched between two layers of a nonwoven spunbond fabric. The chassis mounts an absorbent core and includes six additional colored elastic threads in the rear of the chassis to serve as an indicator of the back side of the product. Like the Depend® products the Always® products also exhibit a somewhat puckered appearance.

Livedo, USA offers an incontinent brief under the trademark LivDry™. That product makes use of a chassis having approximately forty widely spaced transversely extending white spandex elastic strands in panels laminated between two layers of white spunbond fabric, plus an additional eight colored elastic spandex strands in the rear of the product to serve as an indicator of the back side of the product. Like the Depend® products and the Always® products, the LivDry™ products also exhibit a somewhat puckered appearance.

Kimberly-Clark manufactures two other adult incontinence products under the names: Depend Silhouette and Depend Real Fit. Both products employ an elastic melt-blown film fabric-like material that is difficult to process, has higher cost and has limited stretch.

Moreover, many current adult disposable absorbent products, utilize what is known as a fiberized bleached wood fluff pulp and a SAP (Super Absorbent Polymer) mixture for the absorbent core. At low ratios of 30% or less SAP to pulp ratio, the core mixture may or may not be wrapped in an absorbent tissue to prevent the SAP from falling apart or out of the core. At higher levels of SAP at 50% or more, the core must be wrapped to prevent the loose SAP from being shaken out. Also a core adhesive may be added to prevent the heavier SAP particles from being separated from the fluff pulp fibers. The pulp fiber in these products is required to rapidly manage the body fluid exudates until the SAP can desorb the fluff fibers to prepare the fluff fibers for the next exudates. For an adult the amount of exudate is can easily exceed 300 ml. or more delivered over a time period of more than 70 seconds at a rate similar or less than what infants void.

A significant problem with the current absorbent products that contain wood fluff pulp or even wrapped with a tissue or air-laid is in all cases their construction results in a core which feels wet against the body after it has received the voided fluid(s). To address this wet feel, almost all current absorbent product designs employ a distancing layer of synthetic fibers on top of the "wet core" as an attempt to create a "feel drier" layer. This synthetic distancing layer is often called a "fluid transfer layer", "fluid acquisition layer", or "acquisition distribution layer (ADL)" and is typically much smaller than the core that it covers, leaving the edges of the core exposed. Moreover, despite their design goal, such fluid acquisition layers only work to a limited degree. In this regard as the exudate leaves the body at 98 degrees Fahrenheit it quickly drops to about 90 degrees Fahrenheit as it enters the core of the absorbent product. This creates a cooling effect when touched by the skin, which may increase during the time worn. If left on for an extended period of time, the wet product will achieve a thermal equilibrium and equilibrate somewhere between room temperature and about 90 degrees Fahrenheit, depending upon ambient temperature and clothes worn. This difference can be further exacerbated depending upon the thermal conductivity of the materials chosen to absorb the exudate. But in all cases current wood pulp fluff absorbent products will feel wet and/or cold to the skin the longer the product is worn.

The current state of the art product design for the synthetic absorbent cores is based upon a synthetic continuous fiber matrix inter-layered with SAP. For example a polypropylene tow fiber similar to tow used in cigarette filter making was chosen. This material is purchased in a continuous form and is pulled out of the box and proceeds into an air trumpet or similar device or the like, to expand the fiber tow matrix. Then SAP particles are intermixed, adhesive is sprayed into the fiber SAP matrix and the entire matrix is wrapped to result in what is the state of the art of current so-called "pulp-less" core technology. This type of core has the major limitations of a slow absorbency rate. That rate is highly dependent upon the SAP chosen and on the adhesive type and amount required to attach the SAP to the tow fiber matrix. For example, if enough adhesive is provided to ensure that the SAP remains in its desired location within the core, that adhesive may limit the SAP's absorbent swelling due to coating part of the SAP particles. If less adhesive is utilized, while it may permit greater swelling and absorption of the exudate by the SAP, it may allow the SAP particles to fall from their positions in the core to the bottom of the crotch area, rendering it heavier and wetter in the crotch area when voided into and less absorbents at the ends.

Another example of current pulp-less core technology is gluing the SAP to the back sheet or inside the top or body facing sheet. This bonding process may limit the SAP from being fully expanded and utilized in absorbing the exudate. When bonded in such a matter, the SAP may also be applied in continuous rows to provide space for the fluid to travel unhindered. Or the SAP may be intermixed with ground wood pulp fibers of similar size to enhanced fluid movement in this inefficient design.

Current SAP limitations require having to choose between a higher absorbent capacity, with the disadvantage of having slower speed, or a faster SAP with less absorbing capacity. If the current SAPs are mixed, the fast acting SAP will very rapidly swell and may "gel-block" the slower acting, but higher absorption capacity SAP. If gel-blocking occurs, it will limit, or even prevent, the higher capacity SAP from desorbing the faster but lower capacity SAP.

In the past a cellulose acetate fiber core with a single SAP has been developed and commercially available, as has a non-SAP version. Current polypropylene filament tow technology has also been used for the absorbent cores. In this regard, such polypropylene tow cores used in the market today make use of round or oval homo-polymer polypropylene fibers, which provide minimal resistance to fluid flow through the SAP/tow fiber matrix, thereby only providing minimal dwell time for the fluid to be absorbed by the SAP.

While the aforementioned prior art products are generally suitable for their intended purposes, they nevertheless leave something to be desired from the standpoint their ability to absorb voided liquids quickly, easily and effectively without leakage, in an undergarment which is comfortable, thin, aesthetically pleasing and highly concealable under outer clothing. Thus, a need exists for disposable undergarments that address those needs.

The subject invention addresses those needs by providing a undergarment whose chassis includes a much larger number of transversely extending elastic strands, which are spaced closer to one another to provide a significantly improved fit to the wearers body, while at the same time providing a flatter appearance than the puckered look of the prior art incontinent undergarments. Moreover, the chassis mounts an absorbent core which is composed of two sections of SAP for quickly and securely absorbing voided liquid without leakage. To that end, one section of the core, which is located facing the wearer's body, includes a plurality of pockets partially filled with a free, slow acting, but highly absorbent SAP. The other section of the core is located facing away from the wearer's body and includes a plurality of pockets partially filled with a free, fast acting, but lower absorbency SAP. With this construction, liquid voided into the core is initially quickly absorbed by the fast acting SAP section, whereupon the section with the slow acting, but high absorbency SAP desorbs the section with the fast acting SAP to securely contain the voided liquid therein and prevent any leakage out of the core.

SUMMARY OF THE INVENTION

One aspect of this invention there is a disposable absorbent undergarment configured to be worn by a person. The undergarment comprises a chassis and an absorbent core configured for absorbing fluid from the person. The absorbent core has a predetermined width. The chassis comprises a sheet of a cloth-like, non-woven, breathable material. The sheet has an inner surface, a front section, a back section, and an intermediate section located between the front section and the back section. The front section includes a top front edge, a pair of front side edges, and a plurality of elastic threads extending parallel to the top front edge and to each other from one of the pair of front side edges to the other of the pair of front side edges. The back section includes a top back edge, a pair of back side edges, and a plurality of elastic threads extending parallel to the top back edge and to each other from one of the pair of back side edges to the other of the pair of back side edges. The intermediate section comprises a pair of central side edges and a plurality of elastic threads extending parallel to the front top edge, to the back top edge, and to each other from one of the pair of central side edges to the other of the pair of central side edges. Respective ones of the front side edges are secured to respective ones of the back side edges. Each of the pair of central side sections comprises an ergonomically shaped recess forming a respective leg opening for the person. The recesses are spaced apart from each other by a distance which is greater than the predetermined width of the core. The absorbent core is secured on the inner surface of the chassis at the intermediate section between the respective leg openings, with plural ones of the plurality of elastic threads of the intermediate section being cut into separated segments at the location of the core so as not to tend to collapse or buckle the core when the garment is worn by the person.

In accordance with one preferred aspect of the garment of this invention the plurality of elastic threads of the front section extend from a point closely adjacent the top front edge to the intermediate section and are closely spaced to one another, whereupon the front section exhibits a minimally puckered appearance, and wherein the plurality of elastic threads of the back section extend from a point closely adjacent the top back edge to the intermediate section and are closely spaced to one another, whereupon the back section exhibits a minimally puckered appearance.

In accordance with another preferred aspect of the garment of this invention the spacing between immediately adjacent elastic threads is approximately 5 mm.

In accordance with another preferred aspect of the garment of this invention the elastic threads are colored so as to be readily visible from the exterior of the undergarment.

In accordance with another preferred aspect of the garment of this invention the undergarment includes a waistband portion adjacent the top front edge and the top back edge. The waistband portion comprises a plurality of waistband elastic threads extending parallel to the front top edge and to the back top edge. The waistband elastic threads have a greater degree of tension or stretchability than the elastic threads in portions of the chassis between the waistband portion and the crotch section.

In accordance with another preferred aspect of the garment of this invention the elastic threads in the portions of the chassis between the waistband portion and the crotch section exhibit a gradient of tension or stretchability which decreases towards the crotch section.

In accordance with another preferred aspect of the garment of this invention the gradient of tension or stretchability comprises at least three zones of different tension or stretchability.

In accordance with another preferred aspect of the garment of this invention the core comprises a first section and a second section. The first section is formed of at least one layer of porous material configured to permit the migration of liquid therethrough. The at least one layer of porous material of the first section is quilted to form a plurality of first pockets. Each of the first pockets is partially filled with a free, slow acting but high absorption capacity SAP. The second section is located below the first section and has a predetermined width and length. The second section is formed of a layer of porous material configured to permit the migration of liquid therethrough. The porous material of the second section is quilted to form a plurality of second pockets. Each of the second pockets is partially filled with a free, fast acting but lower absorption capacity SAP. The first section of the core and the second section of the core are in fluid communication with each other, with the first section of the core forming a body-facing side disposed confronting the perineum region of the person, whereupon fluid voided by the person flows to the fast acting SAP and to the slow acting SAP, wherein the fluid is absorbed quickly and rapidly by the fast acting SAP, while the slow acting SAP desorbs or takes fluid away from the fast acting SAP as well as absorbing the fluid itself.

In accordance with another preferred aspect of the garment of this invention the core comprises a fluid acquisition layer disposed over the first section of the core.

In accordance with another preferred aspect of the garment of this invention the volume of SAP in at least some of the first pockets is within the range of approximately 25 to 35 percent of the volume of the first pockets, and wherein the volume of SAP in at least some of the second pockets is within the range of approximately 20 to 30 percent of the volume of the second pockets.

In accordance with another preferred aspect of the garment of this invention the core has a predetermined width and length, wherein the second section of the core has a predetermined width and length, and wherein the core comprises an intermediate nonwoven fluid transfer layer, e.g., an airlaid material or the like having a predetermined width which is less than the predetermined width of the first and second sections. The intermediate nonwoven fluid transfer layer is located between the first and second sections to facilitate the fluid transfer between the first and second sections.

In accordance with another preferred aspect of the garment of this invention the first section comprises a first layer of porous material and a second layer of porous material. Each of the first and second layers are configured to permit the migration of a liquid therethrough and are quilted by fixedly secured securement lines to form a plurality of first pockets in the first layer and a plurality of first pockets in the second layer. Each of the first pockets is partially filled with a free, slow acting but high absorption capacity SAP.

Another preferred aspect of this invention is an absorbent core comprising a first section and a second section. The first section is formed of at least a first layer and a second layer. Each of the first and second layers is formed of a porous material configured to permit the migration of liquid therethrough and is quilted by fixedly secured securement lines to form a plurality of first pockets in the first layer and a plurality of first pockets in the second layer. Each of the first pockets is partially filled with a free, slow acting but high absorption capacity SAP, wherein the volume of SAP in at least some of the first pockets of the first layer is within the range of approximately 25 to 35 percent of the volume of the first pockets of the first layer, and wherein the volume of SAP in at least some of the first pockets of the second layer is within the range of approximately 80 to 120 percent of the volume or amount of the SAP is said first pockets of the second layer and within the range of approximately 25-35 percent of the volume or capacity of the first pockets of the second layer. The first section forms a body-facing side disposed confronting the perineum region of the person. The second section is located below the first section and is in fluid communication with the first section. The second section has a predetermined width and length. The second section is formed of a layer of porous material of configured to permit the migration of a liquid therethrough. The layer of the second section is quilted to form a plurality of second pockets. Each of the second pockets is partially filled with a free, fast acting but lower absorption capacity SAP, wherein the volume of SAP in at least some of the second pockets is within the range of approximately 20-30 percent of the volume of the second pockets. The core is configured whereupon fluid voided by the person flows to the fast acting SAP and to the slow acting SAP, wherein the fluid is absorbed quickly and rapidly by the fast acting SAP, while the slow acting SAP desorbs or takes fluid away from the fast acting SAP as well as absorbing the fluid itself.

In accordance with one preferred aspect of the absorbent core the first section comprises a third layer formed of a porous material configured to permit the migration of liquid therethrough and quilted by fixedly secured securement lines to form a plurality of first pockets in the third layer, and wherein the volume of SAP in at least some of the first pockets of the third layer is within the range of approximately 80-120 percent of the volume or amount of SAP of the first pockets of the second layer and approximately 25-35 percent of the volume or capacity of the first pockets of the second layer.

Another preferred aspect of this invention is an absorbent core comprising a first section and a second section. The first section is formed of at least a first layer and a second layer. Each of the first and second layers is formed of a porous material configured to permit the migration of liquid therethrough and is quilted by fixedly secured securement lines to form a plurality of first pockets in the first layer and a plurality of first pockets in the second layer. Each of the first pockets is partially filled with a free, slow acting but high absorption capacity SAP, wherein the SAP in the first section has a "vortex time" in the range of approximately 30 to 90 seconds. As is known in the art the term "vortex time" represents the amount of time that it takes SAP which is mixed with water in a vessel by a spinning stirrer to form a gel to stop the spinning stirrer. The first section forms a body-facing side disposed confronting the perineum region of the person. The second section is located below the first section and is in fluid communication with the first section. The second section has a predetermined width and length. The second section is formed of a layer of porous material of configured to permit the migration of a liquid therethrough. The layer of the second section is quilted to form a plurality of second pockets. Each of the second pockets is partially filled with a free, fast acting but lower absorption capacity SAP, wherein the SAP in the second section has a vortex time of in the range of approximately 3 to 20 seconds, but preferably less than 10 seconds. The ratio of the vortex time of the slow acting SAP of the first absorbent section to the fast acting SAP of the second absorbent section is within the range of approximately 6:1 to approximately 3:1. The core is configured whereupon fluid voided by the person flows to the fast acting SAP and to the slow acting SAP, wherein the fluid is absorbed quickly and rapidly by the fast acting SAP, while the slow acting SAP desorbs or takes fluid away from the fast acting SAP as well as absorbing the fluid itself.

In accordance with one preferred aspect of the absorbent core the first section comprises a third layer is formed of a porous material configured to permit the migration of liquid therethrough and is quilted by fixedly secured securement lines to form a plurality of first pockets in the third layer, with each of the first pockets of the third layer being partially filled with a free, slow acting but high absorption capacity SAP.

Another preferred aspect of this invention is an absorbent core having a longitudinal axis and comprising a first section and a second section. The first section is formed of at least one layer of a porous material configured to permit the migration of liquid therethrough and is quilted by fixedly secured securement lines to form a plurality of first pockets in the at least one layer. Each of the first pockets is partially filled with a free, slow acting but high absorption capacity SAP. Each of the first pockets is diamond shaped has a first pair of diametrically opposed corners and a second pair of diametrically opposed corners, and wherein the first pockets are oriented so that the first pair of diametrically opposed corners extend parallel to the longitudinal axis. The first section forms a body-facing side disposed confronting the perineum region of the person. The second section is located below the first section and is in fluid communication with the first section. The second section is formed of a layer of porous material of configured to permit the migration of a liquid therethrough. The layer of the second section is quilted to form a plurality of second pockets. Each of the second pockets is partially filled with a free, fast acting but lower absorption capacity SAP. Each of the second pockets is diamond shaped has a first pair of diametrically opposed corners and a second pair of diametrically opposed corners, and wherein second pockets are oriented so that the first pair of diametrically opposed corners extend parallel to the longitudinal axis. The core is configured whereupon fluid voided by the person flows in a tortuous path produced by the orientation of the diamond shaped pockets with respect to the longitudinal axis to the fast acting SAP and to the slow acting SAP, wherein the fluid is absorbed quickly and rapidly by the fast acting SAP, while the slow acting SAP desorbs or takes fluid away from the fast acting SAP as well as absorbing the fluid itself.

In accordance with one preferred aspect of the absorbent core the first section comprises a first layer and a second layer. Each of the first and second layers is formed of a porous material configured to permit the migration of liquid therethrough and is quilted by fixedly secured securement lines to form a plurality of first pockets in the first layer and a plurality of first pockets in the second layer. Each of the first pockets in each of the first and second layers is diamond shaped has a first pair of diametrically opposed corners and a second pair of diametrically opposed corners, and wherein the first pockets of the first and second layers are oriented so that the first pair of diametrically opposed corners extend parallel to the longitudinal axis.

In accordance with one preferred aspect of the absorbent core the diamond shaped pockets are square and in the range of approximately 1.5 cm by 1.5 cm to 3.0 cm. by 3.0 cm.

Another aspect of this invention is another absorbent core for an absorbent garment to be worn by a person. The absorbent core has a longitudinal axis and comprising a first absorbent section and a second absorbent section. The first absorbent section is formed of a porous material and has a first pair of longitudinally extending side edges. The first absorbent section comprises first and second layers configured to permit the migration of liquid therethrough. The first layer is disposed over the second layer. Each of the first and second layers is quilted by fixedly secured securement lines to form a plurality of first pockets therein. The first pockets of the first layer are partially filled with a free, slow acting but high absorption capacity SAP. The first pockets of the second layer include outer first pockets located closely adjacent respective ones of the first pair of longitudinally extending side edges and inner first pockets located between the outer first pockets. Each of the outer first pockets is partially filled with a free, slow acting but high absorption capacity SAP. Each of the inner first pockets is partially filled with a free, slow acting but high absorption capacity SAP, with the volume of SAP in the outer first pockets being greater than the volume of SAP in the inner first pockets. The first section forms a body-facing side disposed confronting the perineum region of the person. The second absorbent section is located below the first absorbent section and is in fluid communication with the first section. The second section is formed of a layer of porous material. The layer of the second section is configured to permit the migration of a liquid therethrough and being quilted to form a plurality of second pockets. The second pockets are partially filled with a free, fast acting but lower absorption capacity SAP. The core is configured whereupon fluid voided by the person flows to the fast acting SAP and to the slow acting SAP, wherein the fluid is absorbed quickly and rapidly by the fast acting SAP, while the slow acting SAP desorbs or takes fluid away from the fast acting SAP as well as absorbing the fluid itself.

In accordance with one preferred aspect of the absorbent core of this invention, the first section comprises another layer formed of a porous material and configured to permit the migration of liquid therethrough. The other layer is quilted by fixedly secured securement lines to form a plurality of first pockets therein, with each of the first pockets of the other layer being partially filled with a free, slow acting but high absorption capacity SAP.

In accordance with another preferred aspect of the absorbent core of this invention, the outer first pockets make up approximately two thirds of the width of the first absorbent section.

In accordance with another preferred aspect of the absorbent core of this invention, the absorbent core additionally comprises a fluid transfer or wicking layer disposed between the first absorbent section and the second absorbent section.

Another aspect of this invention is another absorbent core for an absorbent garment to be worn by a person. The core has a longitudinal axis and comprising a first absorbent section and a second absorbent section. The first absorbent section is formed of first layer of a porous material and a second layer of porous material. The first layer is configured to permit the migration of liquid therethrough and is quilted by fixedly secured securement lines to form a plurality of first pockets in the first layer. The second layer is disposed under the first layer and configured to permit the migration of liquid therethrough. The second layer is quilted by fixedly secured securement lines to form a plurality of first pockets in the second layer. Each of the first pockets of the first and second layers is partially filled with a free, slow acting but high absorption capacity SAP. At least some of the first pockets of the second layer are also partially filled with an odor absorbing material. The first layer of the first section forms a body-facing side disposed confronting the perineum region of the person. The second absorbent section is located below the first absorbent section and is in fluid communication with the first section. The second section is formed of a layer of porous material. The layer of the second section is configured to permit the migration of a liquid therethrough and is being quilted to form a plurality of second pockets. The second pockets are partially filled with a free, fast acting but lower absorption capacity SAP. The core is configured whereupon fluid voided by the person flows to the fast acting SAP and to the slow acting SAP, wherein the fluid is absorbed quickly and rapidly by the fast acting SAP, while the slow acting SAP desorbs or takes fluid away from the fast acting SAP as well as absorbing the fluid itself.

In accordance with one preferred aspect of the absorbent core of this invention, the core additionally comprises a fluid transfer or wicking layer disposed between the first section and the second section.

In accordance with another preferred aspect of the absorbent core of this invention, rein the first section comprises another layer formed of a porous material and configured to permit the migration of liquid therethrough. The other layer being quilted by fixedly secured securement lines to form a plurality of first pockets therein, with each of the first pockets of the other layer being partially filled with a free, slow acting but high absorption capacity SAP.

DESCRIPTION OF THE DRAWING

FIG. 1 is an isometric view of one exemplary absorbent undergarment constructed in accordance with this invention and including an aesthetically pleasing, thin chassis and an absorbent core assembly mounted within the chassis;

FIG. 2 is an enlarged top plan view of the absorbent undergarment of FIG. 1, but shown in its laid-flat state immediately preceding the sealing of its marginal edges to complete the undergarment;

FIG. 6 is a top plan view of one exemplary absorbent core assembly of the undergarment shown in FIGS. 1 and 2;

FIG. 7 is a top plan view of one multi-pocketed structure containing slow-acting but high absorbency SAP particles within the pockets thereof, and which structure forms one layer of an upper section of the core assembly shown in FIG. 6;

FIG. 8 is a top plan view of a second multi-pocketed structure containing slow-acting but high absorbency SAP particles within the pockets thereof, and which structure forms a second layer of the upper section of the core assembly shown in FIG. 6;

FIG. 9 is a top plan view of a fluid-transfer or wicking layer forming an intermediate layer of the core assembly shown in FIG. 6;

FIG. 10 is a top plan view of one multi-pocketed structure containing fast-acting but lower absorbency SAP particles within the pockets thereof, and which structure forms a layer of a lower section of the core assembly shown in FIG. 6;

FIG. 11 is a greatly enlarged sectional view, not to scale, taken along line 11-11 of FIG. 6;

DETAILED DESCRIPTION OF PREFERRED EMBODIMENTS

Figure 2A:
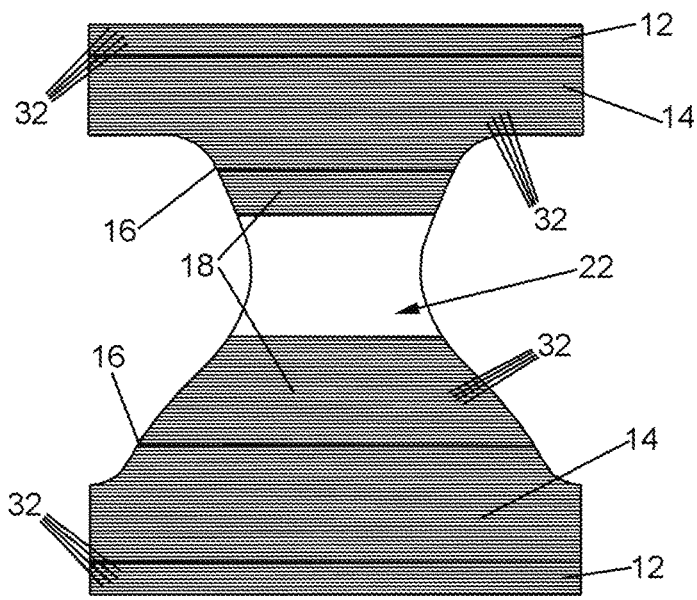
FIG. 2A is an illustration of chassis shown in FIG. 2.

Referring now to the various figures of the drawing wherein like reference characters refer to like parts, there is shown in FIG. 1 one exemplary embodiment of a disposable absorbent undergarment 10 constructed in accordance with this invention. The exemplary undergarment shown is in the form of a brief which is arranged to be worn by a person, e.g., an adult, under clothing to provide excellent fluid absorption and other capabilities in a construction that is comfortable to wear, easy to put on and take off, yet which is extremely thin and aesthetically pleasing so as to be virtually undetectable when worn under clothing. The brief includes a chassis 22 and an absorbent core assembly 24, each of which will be described in detail later. However, before doing that it must be pointed out that while the exemplary undergarment 10 of FIG. 1 is shown and described as being in the form of a brief for adults, it can be readily modified using many of the features which will be described later so that can be used in undergarments other than briefs. Moreover, the core can be used in disposable absorbent products for children and babies, e.g., the core can be used in a chassis of a diaper. In fact, with appropriate modifications the core can be configured for use in a chassis suitable for use on pets. Moreover, and quite significantly, many of the various components of the disposable absorbent article, alone or in combination with each other are novel and provide significant utility for various other type absorbent products, e.g., feminine hygiene pads, panty liners, bandages, etc. Further still, the undergarment may include one or more of an odor reducing system, a treatment system, and a wetness detecting system. Any one or more of the odor reducing system, the treatment system and the wetness detecting system may incorporated in the absorbent core assembly 24 or located in the chassis 22.

Figure 3:
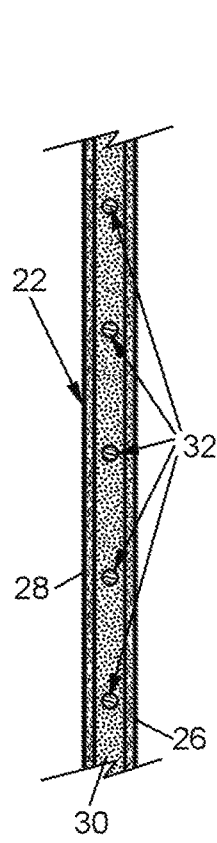
FIG. 3 is an enlarged sectional view taken along line 3-3 of FIG. 2.

The chassis 22 is best seen in FIGS. 1-5 and basically comprises an outer sheet or shell 26 and an inner sheet or shell 28. The outer sheet is formed of a cloth-like, nonwoven breathable fabric, e.g., spunmelt polypropylene, or spunmelt polyethylene, or spunmelt polyester. If desired the outer sheet may be laminated to a barrier film like material, such as a 0.5 to a 1.1 mil polypropylene or polyethylene film. The film should be liquid impermeable to prevent leakage, e.g., an extrusion coated SMS or the like. The inner sheet 26 forms the "body-side" sheet of the chassis and is also formed of a non-woven, breathable material, e.g., spunmelt polypropylene, or spunmelt polyethylene, or spunmelt polyester, or the like. The inner and outer sheets are similarly sized and shaped, with the inner sheet disposed over the outer sheet and adhesively secured thereto by an interposed layer of an adhesive 30, e.g., such as Henkel 901 B construction adhesive or the like construction adhesives typically used in the manufacture of adult and infant disposable absorbent products to form the chassis as best seen in FIG. 3. A large plurality, e.g., approximately one hundred eighteen, of elastic filaments, fibers or threads 32, the details of which will be described later, are secured within the adhesive layer 30 and extend laterally across the full width of the chassis 22, except for a portion of the chassis which forms the crotch section of the undergarment. The elastic threads extend parallel to a transverse axis TX and are closely spaced from one another, e.g., approximately 4-5 mm apart. The elastic threads 32 are normally in a relaxed or un-stretched state when the undergarment is not worn. When worn the elastic threads stretch to cause the undergarment to closely conform to the anatomy of the wearer.

The chassis includes a front or "belly" section 34, a back or "rear" section 36, and an intermediate or crotch section 38. The crotch section 38 is centered about a transverse axis TX A recess 40 is located in the right side edge of the chassis. A similarly shaped recess 42 is located in the left side edge of the chassis. The recesses form respective leg openings 44 (FIG. 1) of the undergarment. The right side recess includes a portion which is located in the front section, a portion that is located in the crotch section and a portion that is located in the rear section. Similarly, the left side recess includes a portion which is located in the front section, a portion that is located in the crotch section and a portion that is located in the rear section. The front section 34 includes a top front edge 46, a right front side edge 48, a portion 50 of the right side recess 40, a top left front side edge 52, and a portion of the left side recess 42. The top front edge 46 is linear, as are the right front side edge and the left front side edges 48 and 52, respectively. The rear section 36 includes a top rear edge 56, a right rear side edge 58, a portion 60 of the right side recess 40, a left rear side edge 62, and a portion 64 of the left side recess 42. The top rear edge 56 is linear, as are the right rear side edge and the left rear side edges 58 and 62, respectively.

As is conventional, the portions of the chassis 22 contiguous with the front side edges 48 and 52 form what are commonly referred to as the front section "ears" of the chassis, while the portions of the chassis contiguous with the back side edges 58 and 62 form the back section ears of the chassis. The respective front section ears of the chassis are secured to the respective back section ears of the chassis, along seal lines 66 by any suitable means, e.g., ultrasonic bonding, thermal bonding, adhesive bonding, etc., to form the undergarment shown in FIG. 1.

The distance between the top front edge 46 and the middle of the crotch section 38, as defined by the transverse axis TX is less than the distance between the top rear edge 56 and the middle of the crotch section, since the front section 34 will have to cover less of the wearer's body than the rear section 36, i.e., the rear section has to cover the wearer's buttocks, whereas the front section only has to cover the wearer's belly and pubic area.

The elastic fibers or threads 32 in the front section 34 extend parallel to each other and to the transverse axis TX from the top front edge 46 down the front section to a point in the crotch section adjacent, e.g., approximately 60 mm from, the transverse axis TX. The elastic fibers or threads 32 in the rear section 36 extend parallel to each other and to the transverse axis TX from the top rear edge 56 down the rear section to a point in the crotch section adjacent, e.g., approximately 60 mm from, the transverse axis TX. The uppermost six or eight elastic threads 32 of the front and rear sections form what can be called the "waistband" 12 of the undergarment 10. The elastic threads of the waistband 12 can be the same gauge as the elastic threads making up the remainder of the chassis, although it is preferable that the elastic fibers forming the waistband are of a heavier gauge to provide a tighter fit at the waistband. For example, the waistband portion may contain 6-8 elastic threads of 800 Decitex (DTEX) Lycra, whereas the remainder of the elastic threads of the chassis are 470-680 DTEX Lycra. While in the preferred embodiment shown, the spacing between all of the elastic threads is constant, e.g., 4-5 mm, that spacing can be different. In this connection, it is contemplated that the elastic threads of the chassis can be configured in a gradient spacing arrangement wherein the fibers at the top of the front and rear sections are spaced closer together than the fibers adjacent the transverse centerline (axis TX) to provide for a better fit for the wearer since it is desirable to have the closest fit to be at the waist. Thus, the spacing between the fibers from the waistband down to the transverse axis TX can gradually increase. Alternatively, one could make use of constant spacing between the elastic threads, but with elastic threads being of decreasing gauge or decreasing stretchability from the waistband to the transverse centerline.

FIG. 2A is an illustration of the chassis shown in FIG. 2, wherein the elastic threads 32 are arranged in zones of decreasing tension or stretchability from the waistband 12 to the point of the chassis at which no longer includes such threads. In the illustration of FIG. 2A there are three such zones. The first or upper zone is the region of the chassis making up the waistband 12. The second or intermediate zone 14 is the region of the chassis from the waistband 12 to an intermediate point 16. The third or lower zone 18 is the region of the chassis from the intermediate point 16 to the point at which the elastic threads 32 end. The elastic threads 32 in the waistband 12 may exhibit a level of stretchability or tension of 250-300 percent. The threads in the middle zone 14 may exhibit a stretchability or tension of 175-250 percent and the threads in the lower zone 18 may exhibit a stretchability or tension of 125-175 percent. It must be pointed out that these ranges are merely exemplary and other ranges can be implemented. In fact, instead of being three distinct zones of decreasing stretchability the elastic threads can be configured so that they exhibit a continuous decrease in stretchability from the waistband 12 until the point at which the elastic threads end.

Irrespective of the gauge and/or spacing and/or stretchability of the elastic threads, it is preferred that those threads be colored so that they can be visible through the nonwoven outer sheet 26. That color can be used to signify the intended user of the undergarment. For example, men's undergarments may make use of blue colored elastic threads. Female undergarments may make use of lavender colored elastic threads. Unisex undergarments may make use of green elastic threads.

It is also preferred, but not mandatory, that the elastic threads making up the waistband in either the front section or the back section not be colored, i.e., be white. By so doing the user can readily determine the proper orientation for putting on the garment. In the exemplary embodiment the elastic bands making up the waistband 12 in the rear section of the undergarment are not colored, i.e., are white.

Inasmuch as the elastic threads in the front and rear sections are very large in number and closely spaced from one another, the chassis 22 of this invention will exhibit a much flatter and less puckered appearance than prior art undergarments that use far fewer and more largely spaced elastic threads. This not only provides a more aesthetically pleasing appearance for the garment, but also results in a garment which when worn is very concealable, e.g., simulating regular, cloth underwear.

As mentioned above, the undergarment includes respective leg openings or cuffs 44 for receipt of the legs of the wearer when the undergarment is worn. The leg openings or cuffs 44 are elasticized so that they will engage the legs of the wearer to form a generally leak resistant interface therebetween. In particular, one preferred embodiment of this invention makes use of three elastic fibers or threads 68 for forming the leg cuffs in the front section 34 of the chassis and three elastic fibers or threads 70 for forming the leg cuffs in the rear section 36 of the chassis. The elastic threads 68 and 70 making up the leg cuffs are preferably of a gauge that is greater than the elastic fibers or threads 32. For example, in one preferred embodiment the elastic fibers 68 and 70 are of 800 DTEX Lycra. The three elastic fibers 68 making up the portion of the leg cuff 44 on the right side of the front section 34 of the chassis extend along and generally parallel to the marginal edge of the cut-out recess 40 on the right side of the chassis from the linear side edge 48 to the transverse axis TX. From that point the leg cuff fibers 68 extend in a concave arc section 72 across the chassis, whereupon the leg cuff fibers 68 extend upward along and generally parallel to the marginal edge of the cut-out recess 42 on the left side of the front section of the chassis up to the linear left side edge 52. Thus, the three leg cuff fibers 68 are arranged in a generally V-shaped configuration. In a similar manner, the elastic fibers 70 making up the portion of the leg cuff on the right side of the rear section 36 of the chassis extend along and generally parallel to the marginal edge of the cut-out recess 40 from the linear rear side edge 58 to the transverse axis TX. From that point the leg cuff fibers 70 extend in a concave arc section 74 across the chassis, whereupon the leg cuff fibers 70 extend downward along and generally parallel to the marginal edge of the cut-out recess 43 on the left side of the rear section up to the linear left side edge 62. Thus, the three leg cuff fibers 70 forming the portion of the leg cuffs in the rear section 36 of the chassis are arranged in a generally V-shaped configuration, albeit slightly different in shape to the leg cuff fibers in the front section of the chassis.

Figure 5:
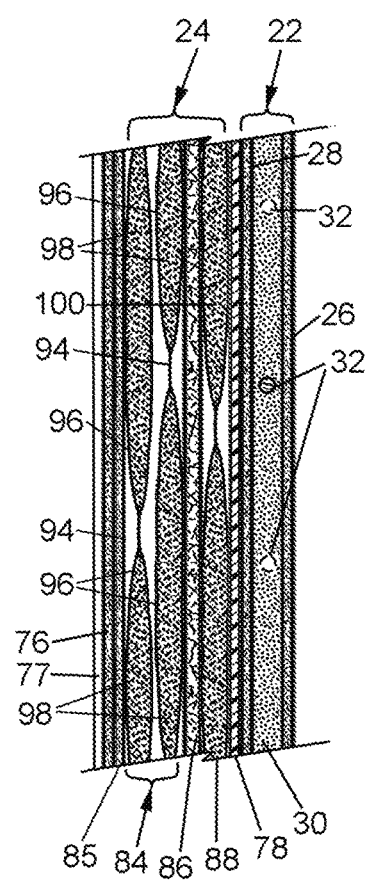
FIG. 5 is an enlarged sectional view taken along line 5-5 of FIG. 2.
Figure 12:
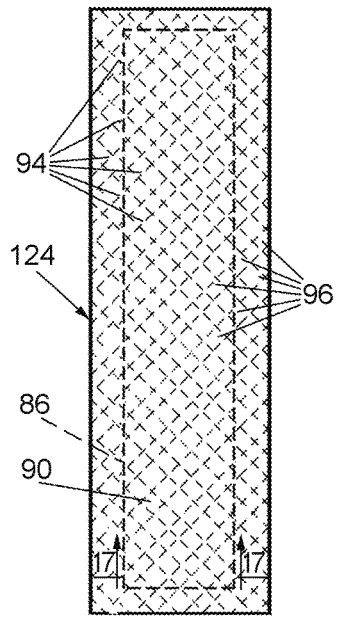
FIG. 12 is a top plan view of an alternative exemplary absorbent core assembly of the undergarment shown in FIGS. 1 and 2.
Figure 13:
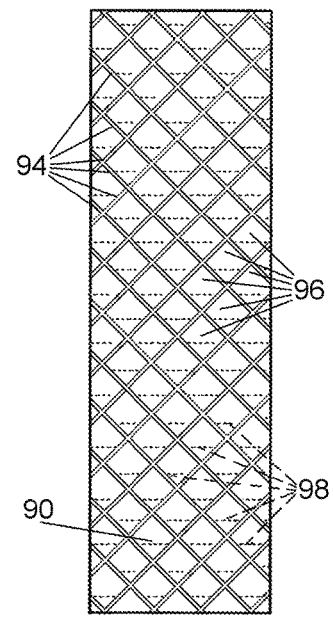
FIG. 13 is a top plan view of one multi-pocketed structure containing slow-acting but high absorbency SAP particles within the pockets thereof, and which structure forms one layer of an upper section of the core assembly shown in FIG. 12.
Figure 14:
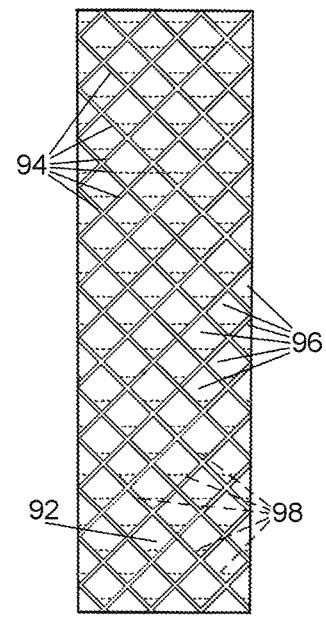
FIG. 14 is a top plan view of a second multi-pocketed structure containing slow-acting but high absorbency SAP particles within the pockets thereof, and which structure forms a second layer of the upper section of the core assembly shown in FIG. 12.
Figure 15:
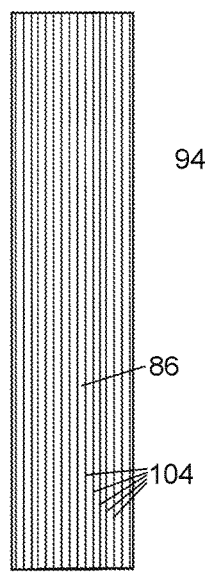
FIG. 15 is a top plan view of a fluid-transfer or wicking layer forming an intermediate layer of the core assembly shown in FIG. 12.
Figure 16:
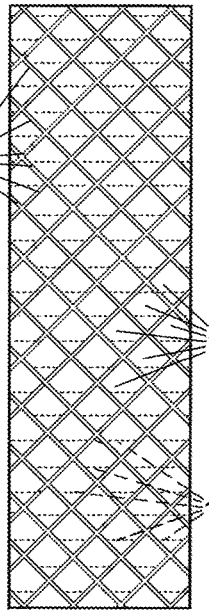
FIG. 16 is a top plan view of one multi-pocketed structure containing fast-acting but lower absorbency SAP particles within the pockets thereof, and which structure forms a layer of a lower section of the core assembly shown in FIG. 12.
Figure 17:
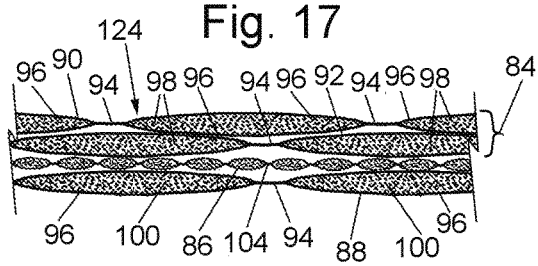
FIG. 17 is a greatly enlarged sectional view, not to scale, taken along line 17-17 of FIG. 12.

The arc shaped sections 72 and 74 of the elastic fibers 68 and 70, respectively, intersect to form a football shaped configuration extending around the transverse axis TX. This creates a somewhat concave or cup shaped pocket at the transverse axis when the chassis is assembled into the undergarment shown in FIG. 1. That concave pocket provides a better and more aesthetically pleasing and comfortable fit, while enhancing concealment of the undergarment when it is worn under outer clothing. It should be noted that in the exemplary embodiment shown the portions of the elastic cuff fibers 68 and 70 forming the arc shaped sections 72 and 74 are not continuous, but rather are sectioned so that there are gaps in those fibers as shown in FIGS. 2 and 5. By so doing the tendency of the garment to pucker in the crotch region, where portions of the core assembly 24 are located, is reduced, while still enabling that portion of the chassis to form a cup shaped pocket.

Figure 4:
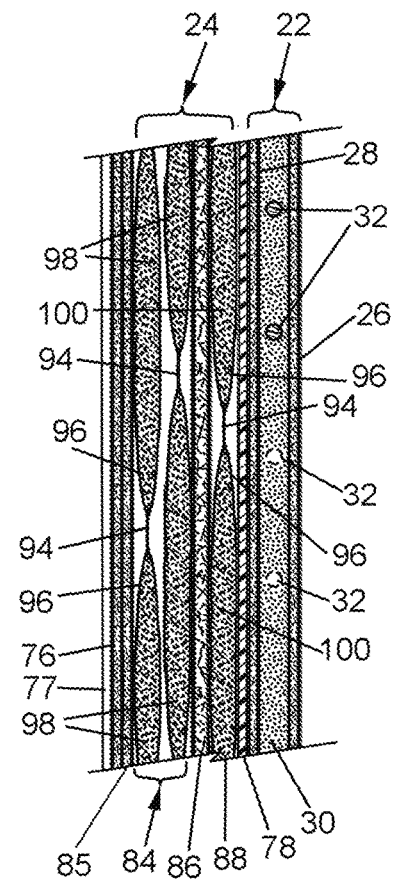
FIG. 4 is an enlarged sectional view taken along line 4-4 of FIG. 2.

The details of the absorbent core assembly 24 will be described later. Suffice for now to state that the absorbent core assembly 24 is a generally thin elongated, e.g., rectangular, body that is fixedly secured between the inner sheet 28 of the chassis and a core assembly cover sheet 76 (FIGS. 4 and 5). The core assembly cover sheet 76 is located closest to the body of the wearer and is made up of a nonwoven material like the outer or inner sheets 26 and 28, respectively, and is larger in length and width than the core assembly 24. The long side marginal edges 77 of the cover sheet 76 are folded over themselves to form marginal flaps 79 (FIG. 2). A plurality, e.g., three, longitudinally extending elastic threads or fibers 82 are disposed between each marginal flap 79 and the immediately adjacent underlying portions of the cover sheet 76. Moreover, the portions of the marginal flaps 79 that are adjacent each end of the cover sheet 76 are adhesively secured to the outer surface of the underlying portions of the cover sheet, with the elastic threads 82 being adhesively secured within the folded over marginal flaps 77. Thus, the elastic threads 82 extend parallel to each other and to the folded edges of the marginal flaps 79. The same adhesive that is used to secure the inner and outer sheets 26 and 28, respectively, together is used to adhesively secure the marginal flaps and the elastic threads 82 in place. The intermediate portions of the marginal flaps, i.e., the portions of the marginal flaps between the ends of the cover sheet 76, are not adhesively secured to the outer surface of the cover sheet so that they will form stand-up leg barriers or gathers 106, as will be described later. The undersurface of the cover sheet 76 is adhesively secured about the periphery thereof to the inner sheet 28 of the chassis 22 by an adhesive, e.g., the same adhesive as used to secure the inner and outer sheets 26 and 28, respectively, together.

A liquid impervious barrier sheet 78 is interposed and secured between the core assembly 24 and the inner sheet 28 of the chassis as also seen in FIGS. 4 and 5. The barrier sheet 78 may be formed of any suitable material, e.g., a film of polypropylene, polyethylene, or polyester. The barrier sheet 78, being liquid impervious, prevents any liquid in the core assembly from leaking out of the core and passing through or wetting the chassis.

As best seen in FIG. 2, the core assembly 24 is centered about a longitudinal central axis LX, but not centered with respect to the transverse axis TX. One end of the core assembly is located in the front section 34 of the chassis, a middle portion of the core is located in the crotch section 38, and the other end of the core is located in the rear section 36. In particular, one end of the core is located in the front section at or just below the right and left side edges 48 and 52, respectively. The opposite end of the core assembly is located in the rear section 36 at or just below the right and left side edges 58 and 62, respectively, whereupon more of the core is located in the rear section of the chassis than is located in the front section of the chassis.

As shown clearly in FIGS. 1, 2 and 4, the portions of the elastic threads 32 which are located in the areas of the chassis where portions of the absorbent core assembly 24 are located are discontinuous or segmented, i.e., they are cut into separated segments so that there are gaps 80 between immediately adjacent segments of each elastic thread. As such those elastic thread segments will not tend to collapse or buckle the core assembly, thereby contributing to the concealability, aesthetics and comfort of the undergarment. The portions of the elastic filaments located outside of the bounds of the core assembly in the back section are not discontinuous to form what can be called "cheek" regions of the chassis that will closely conform to the buttocks of the wearer when the undergarment is worn.

In accordance with one preferred embodiment of the invention, and as clearly shown in FIGS. 1 and 2, the elastic threads 32 located at the core assembly are cut or segmented on a 45 degree bias to create the gaps 80. That bias cut has the effect of creating a somewhat more aesthetically pleasing pattern of broken thread segments than if the elastic threads 32 were cut parallel to the central longitudinal axis LX, since any misalignment of longitudinally cut segments would be readily perceivable and give the appearance of a product that is haphazard.

In addition to the elastic leg cuffs 68 and 70 which are located at the leg openings 44, as mentioned earlier the undergarment 10 includes a pair of upstanding stand-up elasticized leg barriers or gathers 106. Those leg barriers or gathers are conventional in that they extend upward from the undergarment at the top of the core assembly and form a fence along either side of the core assembly. Thus, if there should be a very quick insult (urine release) the upstanding walls trap and direct that insult into the core, rather than let the release flow towards the leg opening. As such, the leg barriers or gathers 106 work in conjunction with the elastic leg cuffs 68 and 70 to prevent leakage of the insult out of the leg openings 44. The leg barriers or gathers 106 are formed by two sets of three elastic threads or fibers 82 (FIG. 2) which are adhesively secured to the core assembly cover sheet 76 closely adjacent the side edges 77 thereof. Each of the elastic fibers 82 extends the full length of the cover sheet 76. The tension applied by those fibers or threads tend to cause the intermediate portions of the core assembly cover sheet 76 to stand up from the core assembly when the garment is in the condition like shown in FIG. 1, i.e., ready to be worn.

Turning now to FIGS. 6-11 the details of the core assembly 24 will now be described. The core assembly is designed to absorb liquids that in some way come out of or exit the body of an adult. While the core assembly 24 has particular utility to be used as a component of an undergarment, e.g., a protective disposable brief, it may be used in other applications.

The absorbent core assembly 24 is a generally planar body of any suitable peripheral shape. In this exemplary case the core assembly 24 is an elongate rectangle. It has a longitudinal axis which is parallel to the longitudinal axis LX and a transverse axis which is parallel to the transverse axis TX. The exemplary embodiment of the core assembly is clearly shown in FIGS. 4, 5 and 11 and basically comprises a first or top absorbent section 84, a fluid transfer or wicking layer 86, and a second or bottom absorbent section 88. Preferably, but not mandatorily, a fluid acquisition layer 85, like those of prior art absorbent undergarments is located between the core assembly cover sheet 76 and the first absorbent section 84. The acquisition layer 85 serves to move the liquid to be absorbed linearly across its area to spread it out across the core assembly. One exemplary embodiment of a fluid acquisition layer that can be used in this invention is through air bonded ADL 40 GSM which is 12.1 cm wide. Other materials can be used for the fluid acquisition layer. For example, Shalag STAPPEL40 ADL, STA1PBL40 or STA2PBL38m sold by Shalag US, Inc. or a similar material produced by WPT Corporation or other suppliers of similar ADL nonwoven materials. Such a material is identified by the vendor as being 40 grams per square meter (GSM) basis weight 100% Polyester White. Other similar airlaid acquisition layer materials incorporating polypropylene, polyethylene bi-component fibers or the like used in the industry can be used, with a basis weight ideally of 40 GSM+/−10 GSM, although usage as low as 20 GSM or up to 100 GSM is infrequently used. Another alternative is to use a 3D film such as that available from Tredegar Film Products under the trademark AquiDry Plus 120. In any case the fluid acquisition layer is preferably coextensive in size and shape to the first absorbent section 84.

The first or top absorbent section 84 is of elongated rectangular shape and is provided to move the liquid linearly and is in the form of at least one, and preferably two or more quilted layers. In the preferred embodiment shown herein the first absorbent section 84 is made up of two quilted layers, namely a first layer 90 and a second layer 92 (shown in FIGS. 7 and 8, respectively). Each of those layers is in the form of a pair of non-woven sheets which are fixedly secured together along intersecting seal or embossed lines 94 to form a plurality of diamond shaped enclosed pockets 96 between the intersecting embossed lines. The first layer 90 of the first absorbent section 84 is in the form of a plurality of first pockets 96, and the second layer 92 is in the form of a plurality of first pockets 96. The seal lines 94 can be made by any suitable technique, e.g., ultrasonic welding, thermal welding, adhesive securement, etc.

Each first pocket 96 is of a square shape, e.g., approximately 1.5 cm. by 1.5 cm., with the width of each of the intersecting seal lines being approximately 1 mm. If desired, the first pockets can be larger in size, e.g., up to 3.0 cm by 3.0 cm. or more.

The first pockets 96 are oriented so that two of their diametrically opposed corners extend parallel to the longitudinal axis of the core assembly 24, while the other two diametrically opposed corners extend transverse or perpendicular to that axis. Each pocket is partially filled with free SAP, as will be described later. As should be appreciated by those skilled in the art, the orientation of the pockets with respect to the longitudinal axis establishes a tortuous flow path for fluid along the longitudinal axis of the core. Moreover, the quilted nature of the two layers 90 and 92 of first section 84 renders the free SAP particles of the layers of that section resistant to migration with respect to the core assembly and thus obviates the need for adhesives to bond to the SAP particles to prevent their migration.

The nonwoven sheets making up the two layers of the first absorbent section can be a non-woven, liquid pervious material, e.g., 15+/−5 GSM basis weight hydrophilic spunbond nonwoven polypropylene or the like that is 12.1 cm wide. One particularly suitable nonwoven is available from PGI Nonwovens under code # B0305 white SBPP hydrophilic polypropylene spunbond. At minimum the upper body side layer is hydrophilic where the bottom layer may be similar for ease of manufacturing. Alternatively, it could be hydrophobic or a barrier film.

Each of the first pockets 96 of the layers 90 and 92 of the first absorbent section 84 contains a free, high capacity, but slow absorbing SAP 98, with each first pocket being filled to less than half of its volume or capacity, as indicated by the broken lines in the pockets shown in FIGS. 7 and 8, and preferably within the range of approximately 25 to 35 percent of its volume or capacity. In particular, in accordance with one preferred aspect of this invention the amount or volume of SAP 98 in at least some of the first pockets 96 of the first layer 90 is within the range of approximately 25 to 35 percent of the volume or capacity of those first pockets.

Moreover, the amount or volume of SAP 98 in at least some of the first pockets 96 of the second layer is within the range of approximately 80 to 120 percent of the amount or volume of the SAP 98 in the first pockets of the first layer and within 25-35 percent of the volume or capacity of the first pockets of the second layer. To that end, each pocket 96 encapsulates approximately 0.02 to 0.05 grams of SAP, or approximately 100 to 196 grams of SAP per square meter.

The partial filling of the pockets with the high capacity, but slow absorbing SAP 98 serves to allow for the expansion and swelling of the SAP when in contact with the liquid to be absorbed, e.g., urine. If the pockets 96 were filled with significantly more SAP 98, such as greater than 0.10 grams per pocket, the SAP would be constrained in its ability to swell and thus unable to absorb additional fluid. In some instances it may be appropriate to underfill the pockets employing 0.03 grams or even 0.02 grams to ensure maximum utilization at a slightly reduced capacity. It should be pointed out that other size pockets than those described above are contemplated. For example, one can increase the amount of SAP 98 per pocket by employing larger pockets. In each case, the ratio of SAP to the pocket size preferably should not exceed approximately 0.44 grams per 1 square cm. per pocket. If larger pockets are contemplated, then the same ratio of weight per unit area should be applied.

In any case, it is preferred that the vortex time of the high capacity, but slow absorbing SAP 98 be relatively high, e.g., approximately 30 to 90 seconds or more to ensure that all of the liquid voided by the user is absorbed in that section of the core assembly as will be described later. In accordance with one exemplary embodiment of this invention SAP 98 can be BASF T-9900 available from BASF Corporation, or any other suitable SAP.

If desired, the two layers 90 and 92 of first absorbent section 84 can have one or two layers of a nonwoven interposed between the layers 90 and 92. The use of such a layer of layers of nonwoven interposed between the layers 90 and 92 should serve to increase the void space to allow for faster fluid flow into more pockets and layers.

The fluid transfer or wicking layer 86 is best seen in FIG. 9 and serves to aid in transporting voided liquid by wicking or the like. In particular the layer 86 is configured to aid in allowing the liquid to linearly wick along the longitudinal axis LX so that it assists in moving the liquid to be absorbed, e.g., urine, from the central middle area of the core where the liquid is first insulted to the ends of the core where that liquid may not fully reach and to allow that liquid to pass through it into the second absorbent section 88. In the exemplary embodiment, the wicking layer is an airlaid tissue approximately 100 GSM. One particularly suitable material for the wicking layer is available from Domtar/EAM Corporation under the trademark Nova Thin and is described as White Fibrous Web of 100 GSM basis weight. The wicking layer has a corduroy or corrugated embossing pattern that is employed to further assist wicking. The corrugations or corduroy pattern is formed by a plurality of closely disposed parallel seal lines 104 made by any suitable technique, e.g., ultrasonic welding, thermal welding, adhesive securement, etc. The wicking layer is also of an elongated rectangular shape, but preferably of a narrower width, e.g., approximately 5.1 cm wide, than the first and second sections 84 and 88, respectively, for reasons to be described later. The wicking layer is not bonded, also for a reason to be described later. Moreover, the wicking layer may be in the form of plural layers to provide the desired wicking properties. The wicking layer may also have visible holes, of 5 mm in size or larger, added to further enhance fluid pass-through.

The second or bottom absorbent section 88 is preferably coextensive in size and shape to the first or top absorbent section 84 and is configured to be disposed away from the wearer when the undergarment is worn. The second absorbent section 88 is constructed somewhat similarly to the first absorbent section 84, but is in the form of a single quilted layer. That layer is formed in the same manner as each of the layers of the first absorbent section, i.e., it comprises a pair of non-woven sheets of the same material as the sheets of the first absorbent section and which are fixedly secured together along intersecting seal or embossed lines 94 to form a plurality of diamond shaped enclosed second pockets 96 between the intersecting embossed lines like the pockets 96 of the first absorbent section 84. The second pockets 96 of the second absorbent section 88 can be of the same size as the first pockets of the first absorbent section, e.g., 1.5-3.0 cm. square, or may be of a different size, e.g., smaller, than the first pockets of the first absorbent section 84, but still within that range, to permit greater expansion of the high fluid absorption capacity of the SAP 98.

Each of the second pockets 96 of the second absorbent section 88 is partially filled with a free, fast acting but lower absorption capacity SAP 100. In particular, each second pocket is filled to less than half of its volume or capacity, and preferably within the range of approximately 20-30% of its volume or capacity. The vortex time of the fast acting but lower absorption capacity SAP 100 is much quicker than the vortex time of the slow acting but high absorbency SAP 98. Thus, for example the SAP 100 may have a vortex time in the range of approximately 3-20 seconds. Moreover, the ratio of the vortex time of the slow acting SAP 98 of the first absorbent section to the fast acting SAP 100 of the second absorbent section should be anywhere in the range of approximately 6:1 to 3:1, with the higher ratio being preferred. Thus, for example, one preferred vortex time for the SAP 98 is at least 60 seconds, with the vortex time for the fast acting SAP to be 10 seconds or less. In accordance with one exemplary embodiment of this invention the fast acting SAP 100 can be Aqua Keep type BA40B available from Sumitomo Seika Chemicals Co., Ltd., or the like. That product has a very fast vortex time, e.g., approximately 3 to 10 seconds.

Like the first absorbent section, the quilting of the second section renders the SAP of the second absorbent section resistant to migration with respect to the core assembly without requiring adhesives to bond to the superabsorbent particles to prevent their movement or migration.

Each pocket 96 of the second absorbent section 88 encapsulates approximately 0.02 to 0.04 gm of the SAP, or approximately 150 GSM. Since the pockets are only partially filled, they like the pockets of the first absorbent section 84, to allow for the expansion and swelling of the superabsorbent polymers when in contact with the fluid. If the pockets 96 of the second section were filled with significantly more SAP, such as greater than 0.06 gm per pocket, the SAP particles would be constrained in their ability to swell and thus unable to absorb additional fluid. However, other size pockets may be contemplated to increase the amount of SAP per pocket by employing larger pockets. In each case, the ratio of SAP 100 to the pocket size preferably should not exceed approximately 0.16 gm per 1 square cm per pocket. If larger pockets are contemplated, then the same ratio of weight per unit area should be applied.

The fast acting SAP 100 may have a tendency to shatter somewhat during the processing and formation of the section 88. Thus, to minimize this potential problem, a lubricant, such as mineral oil can be added to the SAP 100, the mineral oil being in the range 0.1% to 5%; and preferably 0.1 to 1.0%. Moreover, one may add moisture to the SAP 100 of the bottom section 88 during the processing and formation of that section to reduce dusting. The result of such action is that the SAP 100 of the bottom section 88 has a higher moisture content than the SAP 98 of the top section 84. Furthermore, the inherent nature of SAP 100 of the bottom section allows one to add some of the slower acting SAP 98 like in the first section 84 to fast acting SAP 100 in the second or bottom section to minimize or prevent gel blocking up to 20%. Further still, if desired, the nonwoven material making up the bottom sheet of the quilted second section 88 on may by colorized or printed on bottom by adding an SMS or nonwoven or poly or pigmented specs to SAP for the purpose of indicating the bottom of the absorbent core from the top. This is to eliminate the possibility of reversing the absorbent structure, which would result in a non-functional absorbent core.

The layers 90 and 92 of the first section 84, and the single layer of the second section 88 of the core assembly are fixedly secured together along their marginal (longitudinal) edges by respective seal lines, with the wicking layer interposed between the first and second sections to form a composite core assembly. Those seal lines can be formed by any suitable technique, e.g., ultrasonic welding, thermal welding, adhesive securement, etc. The most desirable process is to ultrasonically bond the components together with a 2 mm wide intermittent bond pattern running down the sides of the composite core assembly and spaced about one cm. from each edge, e.g., somewhat like a railroad track with approximately four bond points or bars per cm. The fact that the wicking layer 86 is narrower than the first and second sections assists in bonding the components of the core assembly together. Moreover, being narrower, the wicking layer 86 enables fluid voided by the person wearing the undergarment 10 to spill over the side edges onto the underlying second absorbent section, thereby facilitating fluid transfer to that section.

With the absorbent core assembly 24 located in the undergarment, when the undergarment is worn the absorbent core assembly forms a body-facing side of the undergarment confronting the perineum region of the wearer. Thus, when the wearer voids, that urine flows into the first absorbent section 84 to the fast acting SAP 98 located in the pockets 96 of the top layer 90 of that section, from whence it flows into the bottom layer 92 of that section and through that layer. Since the SAP 98 in the top section 84 is slow acting, the voided urine quickly flows out of the top section 84 into the underlying wicking layer 86, whereupon it is dispersed across the area of the wicking layer, through it and over its marginal edges to the underlying second absorbent section 88. It is in the second absorbent section where the liquid is absorbed quickly and rapidly by the fast acting SAP 100 located in the pockets of the second absorbent section, while the slow acting SAP desorbs or takes liquid away from the fast acting SAP as well as absorbing the liquid itself. The wicking layer 86 also serves to enhance the fluid transfer from the lower faster absorbent second absorbent section 88 into the upper slower first absorbent section 84.

In order to improve fluid movement through the entire composite absorbent core, it is preferred that the embossed pockets of the first and second absorbent sections are not aligned directly with respect to each other. Rather, they are offset in a direction parallel to the longitudinal axis LX and/or in a direction parallel to the transverse axis TX or in directions parallel to both the longitudinal axis and the transverse axis. This allows for improved fluid migration not only in the longitudinal and transverse directions, but also in a direction perpendicular to the plane of the core assembly. In FIGS. 12-17 there is shown an alternative embodiment of the core assembly 124 wherein the pockets of the first and second sections are not coincident, but rather are offset from each other. In the interest of brevity the details of the construction of the components of the core assembly 124 which are common to the core assembly 24 will be given the same reference numbers and their arrangement and operation will not be reiterated.

While the core assembly 124 offers some advantages from the standpoint of facilitating fluid movement through it, in the interest of ease and simplicity of manufacturing the core assembly, reduced capital costs and concomitant consumer savings, the embossed pockets of the first and second may be directly aligned under each layer and under each other like the core assembly 24.

As should be appreciated by those skilled in the art the quilted construct of the core assemblies of this invention functions via what can be called a "compartment spill over phenomena". In particular, the liquid to be absorbed when brought to the each section of the core will fill up the SAP contained in a compartment (pocket) of that section, whereupon the compartment and the SAP in it will swell. Once the SAP in that compartment is fully utilized (e.g., has swelled to its maximum), the liquid then "spills over" to the adjacent compartments. As mentioned above, the ultrasonically formed diamond shaped pockets or compartments 96 of the first absorbent section and the second absorbent section have approximately a 1 mm space between them as a result of the width of their respective intersecting fixedly secured seal lines 94. This aids in liquid movement, along the voids in the core assembly adjacent those seal lines as shown in the cross-sectional view of FIGS. 11, 17 and 18. The wicking layer 86 also enhances liquid movement as does the unaligned nature of the compartments or pockets. The addition of a topmost body side acquisition layer 85, further aids fluid transfer to assist fluid in the spill over from one SAP containing compartment or pocket to the next.

Moreover, by making use of two layers 90 and 92 of the first absorbent section 84, the core assembly 24 can use less SAP 98 in each of the pockets 96 of the first section than would be used if the first section included only a single quilted layer. As such, with less SAP 98 in a given pocket there is sufficient room for the SAP 98 to expand in the pockets so that it can be fully utilized to desorb the SAP from the second absorbent section. While it is desirable to use the least amount of SAP in the pockets of the first absorbent section for economic reasons, the amount used must be able to be fully utilized to achieve the desired absorption rate and capacity. Thus, it is preferred that the SAP 98 in each of the two layers 90 and 92 of the first absorbent section is within the aforementioned desired range of pocket fullness and that the SAP has a vortex time of in the range of 30-90 seconds to be able to fully desorb the liquid from the second absorbent section. Moreover, that configuration maximizes SAP performance and enables efficient and effective transfer of liquid introduced into the core assembly through each of the two layers of the first absorbent section into the second absorbent section, without any tendency for the SAP 98 of the first absorbent section to impede the flow of liquid into the second absorbent section as could result from "gel blocking". As is known "gel blocking: occurs when the surface of the SAP in a section that comes into contact with the liquid first swells and blocks the lower levels of SAP of that section from fully absorbing to their maximum capacity. By using less SAP in each pocket, but by using more pockets via the two layer construction of the first absorbent section, the occurrence of gel blocking is minimized, if not eliminated. Thus, the liquid introduced into the core assembly can quickly pass through the first absorbent section to be wicked into the second absorbent section, where it is quickly absorbed by the SAP of the second absorbent section, and from whence that liquid can go back to the first absorbent section where that liquid is slowly absorbed, thereby desorbing the second absorbent section, so that all of the liquid is trapped in the core assembly to keep the wearer dry.

Figure 18:
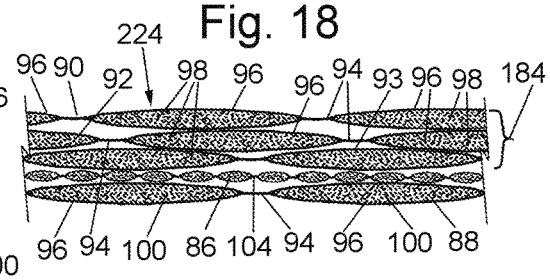
FIG. 18 is an enlarged sectional view like that of FIG. 17, but showing yet another alternative exemplary embodiment of a core assembly constructed in accordance with this invention.

If a higher capacity absorbent core is desired, additional SAP layers like those of the first section could be added to the construct. Thus, for a higher capacity brief, e.g., one suitable for overnight wearing, the first absorbent section may include three quilted layers, each of the three quilted layers being constructed similarly to the two quilted layers 90 and 92 described above. That alternative embodiment of the core assembly is shown in FIG. 18 and is designated by the reference number 224. The core assembly 224 is similar to the construction of the core assembly 124 shown in FIG. 17, except that the first absorbent section 184 includes three quilted layers. In particular, the first section 84 includes a first layer 90, a second layer 92, and a third layer 93. In the interest of brevity the details of the construction of the components of the core assembly 224 which are common to the core assemblies 24 and 124 will be given the same reference numbers and their arrangement and operation will not be reiterated. The third layer 93 is constructed similarly to the layers 90 and 92 and is also partially filled with a slow acting high absorbency SAP 98, wherein the volume or amount of SAP 98 in at least some of the first pockets of the third layer 93 is within the range of approximately 80-120 percent of the volume or amount of SAP 98 in the first pockets of the second layer 92 and within the range of approximately 25-35 percent of the volume or capacity of the first pockets of the third layer 93.

Figure 19:
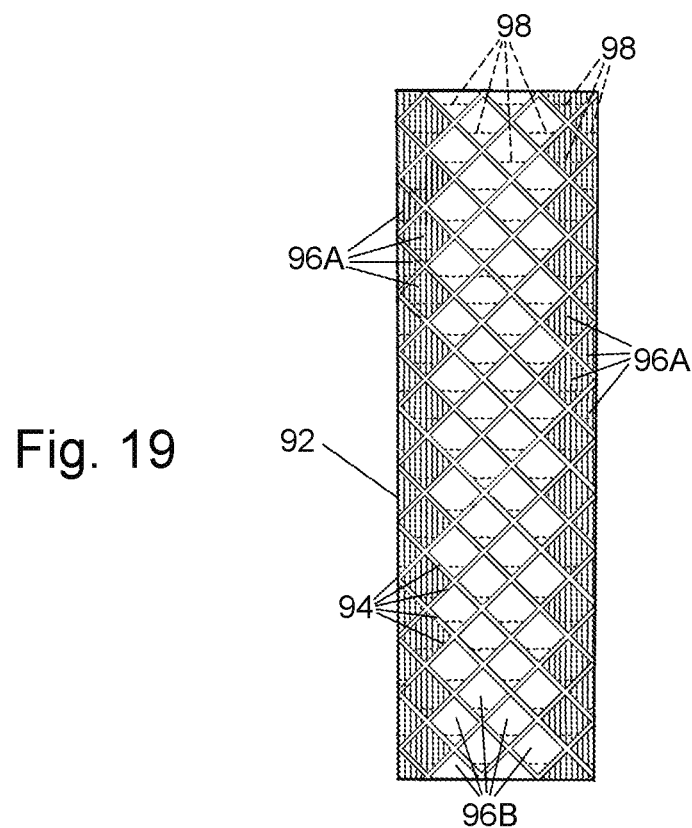
FIG. 19 is a top plan view, like FIG. 7, but showing an alternative multi-pocketed structure containing slow-acting but high absorbency SAP particles within the pockets thereof, and which structure forms one layer of an upper section of yet another alternative embodiment of a core assembly constructed in accordance with this invention.

It should be noted that the core assemblies as described heretofore make use of the same amounts of SAP in the pockets of each layer of the first absorbent section. That is merely exemplary. Thus, for example, it is contemplated, that the core assembly may be constructed to have stripes or zones of pockets with higher and lower concentrations of the slow acting, but high absorbency SAP 98 in a layer of the first absorbent section 84, with higher concentrations adjacent the long side marginal edges. Such an arrangement should deter the leakage of liquid out the sides of the core assembly and is shown in FIG. 19. In particular, in FIG. 19 the pockets located adjacent the long side marginal edges of the core assembly, which are designated as 96A, and which are shown shaded by closely spaced vertical lines are filled with a higher concentration or amount of the SAP 98 than the pockets located between the pockets 96A. The pockets filled with less SAP are designated by the reference number 96B. Thus, as can be seen the pockets 96A form two stripes or zones extending along the marginal edges of the core assembly. Each stripe of the higher concentration of SAP 98 is preferably approximately ⅓ the width of the core assembly. That is merely exemplary and the stripes making up the higher concentration and lower concentration of SAP 98 can be of different widths.

In any case, if stripes or zones of different concentrations of SAP 98 are used, the amount of SAP 98 within the pockets 96A and 96B should still be within the ranges as discussed earlier. Moreover, if the core assembly is constructed like the core assembly of FIG. 17 it is preferred that the layer making use of the stripes or zones of different concentrations of the SAP 98 will be in the second layer 92. If the core assembly making use of a layer of stripes or zones of different concentrations of the SAP 98 is constructed like the embodiment of FIG. 19 the striped or zoned pockets of higher and lower concentration could be in either or both of the second layer 92 and the third layer 93, but preferably be in the second layer 92. In any case, it is preferred that the first or upper layer 90 should not include stripes or zones of higher and lower concentrations of the SAP 98 since that layer faces the body and hence should be kept as dry as possible.

As should be appreciated by those skilled in the art, the use of a layer of different concentrations of SAP 98 in the first absorbent section should not deter the transfer of the liquid insult, e.g., the urine voided, quickly through the first absorbent section into the second absorbent section, since the SAP 98 in the first absorbent section does not absorb liquid quickly.

It is also contemplated that the subject invention can use less expensive inorganic additives to maximize SAP performance. Since the goal of the assembly core of this invention is to allow all the SAP particles of each section to achieve their maximum absorbent capacity, inorganic additives such as high porosity Zeolites, Upsalite, microspheres or other inorganic materials that do not swell or add to the gel blocking phenomena may be included with the SAP of the core. Another approach in lieu of the use of such inorganic additives, or an additional approach to using such additives, is to utilize an acquisition layer, such as a 40 gm Shalag ADL or similar materials from Shalag US, Inc. or similar materials available from WPT Corporation or others may be disposed underneath the second absorbent section of the core. In addition, a second wicking layer could be added between the first and second absorbent layers, if desired.

Further still, since the fast acting SAP 100 of the second absorbent section has a very rapid vortex time, in some cases, and it may have a tendency to gel block, particularly those particles of SAP 100 located closest to the surface of the body of SAP particles within a pocket as opposed to those particles of SAP 100 located in the interior of that body of SAP. In such a case, those interior particles of SAP 100 may not have a chance to absorb the fluid insult. To address this problem, a "caking inhibitor" or "flow agent", may be added in the pockets containing the fast SAP 100 and blended with the SAP in those pockets. The caking inhibitor or flow agent can take the form of calcium sulfate, magnesium carbonate, diatomaceous earth, kaolin, calcium silicate, or the like. Also hollow glass or plastic microspheres, such as those manufactured by 3M could also act as inert flow agents. In any case, the caking inhibitor or flow agent may make up 5 to 20% of the volume of the SAP 100 within the pocket and should preferably have a similar or larger particle size than particles of the SAP 100. In this regard, the SAP 100 has a distribution in microns of less than 11% below 250 microns, approximately 73% between 250 and 500 microns and approximately 16% greater than 500 microns with none greater than 850 microns. Thus, it is contemplated that the anti-caking agent should have a particle size of greater than 250 microns, but probably less than 850 microns.

In the interest of controlling or reducing odor, an odor controlling or odor reducing agent, such as Zeolites, EDTA, enzymes such as amylases, lipases, proteases or the like, and commercially available products such as FEBREZE® odor eliminator, ZERO ODOR®, etc., and combinations thereof, and may be included in some or all of the first pockets 96 of the first absorbent section. Being very porous Zeolite will trap odors. However, when a Zeolite it becomes wet its odor absorbing abilities decrease. Since a Zeolite odor reducing agent will be located within pockets 96 in which the high capacity SAP 98 is located, that SAP will desorb moisture from the Zeolite and thus allow it to function to reduce odors over an extended period of time. In the interest of keeping the wearer of the undergarment 10 dry, it is preferred that the Zeolite odor reducing agent is not located in the layer 90 since that layer is located closest to wearer when the undergarment 10 is worn. Thus, if the first absorbent section of the core assembly includes two quilted layers 90 and 92, like that of FIG. 17, the Zeolite odor reducing agent should be located in the layer 92. If the first absorbent section of the core assembly includes three quilted layers 90, 92, and 93, like that of FIG. 18, the Zeolite odor reducing agent should be located in either or both of the layer 92 and 93, although it is preferred that it be located in the layer 92.

Absorbent cores constructed in accordance with this invention, such as those described above or variations thereof, could be used in lieu of an absorbent core that is employed in current existing absorbent products. For example, core assemblies constructed in accordance with this invention can be used in adult incontinence products (e.g., briefs, panties, pads, etc.), infant absorbent garments (e.g., diapers), sanitary napkins, a feminine napkins, panty liners, or any other product arranged to be worn by a being to absorb liquids from the being. Moreover, while the pockets 96 of the two sections 84 and 88 of the core assembly are shown as being diamond shaped, with all of the pockets being the same size that is merely exemplary. Thus, it is contemplated that other shaped pockets can be used for either section 90 or 92, or both sections 90 and 92. In fact, it is contemplated that the pockets of the two layers 90 and 92 be of different shapes, if desired. Further still the core assembly can be configured so that it includes high and low stripes of SAP within each or any of the layers of the core assembly. Moreover, the SAP can have different concentrations of SAP within the stripes. This can be +/− least 25% from high to low or as much as 75% from high to low). Dependent on the amount of fluid movement desired, these stripes can be lined up peak-to-peak or peak-to-valley.

As should be appreciated from the foregoing the cores of this invention as described above make use of at least two sections, each of which is of a quilted construction including plural pockets. Moreover, each of the pockets is hollow and is partially filled with SAP. The SAP may be in the form of particles or fibers or any other form of SAP which is free or unsecured. The pockets serve to hold the SAP therein to prevent migration of the SAP through the core. It is, however, contemplated that for some applications an adhesive could be used in the pockets to thereby hold the SAP in place. That alternative configuration provides an additional means, in addition to the pockets, for preventing the SAP from migrating through the core.

Without further elaboration the foregoing will so fully illustrate our invention that others may, by applying current or future knowledge, adopt the same for use under various conditions of service.

We claim:

1. A disposable absorbent undergarment configured to be worn by a person, said undergarment having a central longitudinal axis and comprising:
an absorbent core assembly centered on said central longitudinal axis and having a pair of sides extending parallel to said central longitudinal axis, said absorbent core assembly being of a predetermined width between said sides, and being configured for absorbing fluid from the person; and
a chassis comprising a sheet of a cloth-like, non-woven, breathable material, said sheet having an inner surface, a front section, a back section, and an crotch section located between said front section and said back section, said front section including a top front edge, a pair of front side edges defining therebetween the width of said front section, and a plurality of linear elastic threads extending parallel to said top front edge and to each other completely across said width of said front section from one of said pair of front side edges to the other of said pair of front side edges, said back section including a top back edge, a pair of back side edges defining therebetween the width of said back section, and a plurality of linear elastic threads extending parallel to said top back edge and to each other completely across said width of said back section from one of said pair of back side edges to the other of said pair of back side edges, said crotch section comprising a pair of central side edges defining therebetween the width of said crotch section, the maximum width of said crotch section being less than said width of said front and back sections, said crotch section having and a plurality of linear elastic threads extending parallel to said front top edge, to said back top edge, and to each other completely across said width of said crotch section from one of said pair of central side edges to the other of said pair of central side edges, respective ones of said front side edges being secured to respective ones of said back side edges, each of said pair of central side sections comprising an ergonomically shaped recess forming a respective leg opening for the person, said recesses being spaced apart from each other by a distance which is greater than said predetermined width of said absorbent core assembly, said absorbent core assembly being secured on said inner surface of said chassis at said crotch section and centered on said central longitudinal axis between said respective leg openings with plural ones of said plurality of linear elastic threads of said crotch section at said absorbent core assembly being cut into a plurality of separated segments extending across the entirety of said absorbent core assembly from a point adjacent one of said pair of sides to a point adjacent the other of said pair of sides whereupon some of said plurality of separated segments extend through said central longitudinal axis and others of said plurality of separated segments are located immediately adjacent said central longitudinal axis, said plurality of separated segments being configured so as not to tend to collapse or buckle said absorbent core assembly when said garment is worn by the person.

2. The undergarment of claim 1, wherein said plurality of elastic threads of said front section extend from a point closely adjacent said top front edge to said intermediate section and are closely spaced to one another, whereupon said front section exhibits a minimally puckered appearance, and wherein said plurality of elastic threads of said back section extend from a point closely adjacent said top back edge to said intermediate section and are closely spaced to one another, whereupon said back section exhibits a minimally puckered appearance.

3. The undergarment of claim 2, wherein the spacing between immediately adjacent elastic threads is in the range of approximately 4-5 mm.

4. The undergarment of claim 2, wherein said elastic threads are colored so as to be readily visible from the exterior of said undergarment.

5. The undergarment of claim 1, wherein said undergarment includes a waistband portion adjacent said top front edge and said top back edge, said waistband portion comprising a plurality of waistband elastic threads extending parallel to said front top edge and to said back top edge, said waistband elastic threads having a greater degree of tension or stretchability than said elastic threads in portions of said chassis between said waistband portion and said crotch section.

6. The undergarment of claim 5, wherein said elastic threads in said portions of said chassis between said waistband portion and said crotch section exhibit a gradient of tension or stretchability which decreases towards said crotch section.

7. The undergarment of claim 6, wherein said gradient of tension or stretchability comprises at least three zones of different tension or stretchability.

8. The undergarment of claim 1, wherein said absorbent core assembly comprises a first section and a second section, said first section being formed of at least one layer of porous material configured to permit the migration of liquid therethrough, said at least one layer of porous material of said first section being quilted to form a plurality of first pockets, each of said first pockets being partially filled with a free, slow acting but high absorption capacity SAP, said second section being located below said first section and having a predetermined width and length, said second section being formed of a layer of porous material configured to permit the migration of liquid therethrough, said porous material of said second section being quilted to form a plurality of second pockets, each of said second pockets being partially filled with a free, fast acting but lower absorption capacity SAP, said first section of said absorbent core assembly and said second section of said absorbent core assembly being in fluid communication with each other with said first section of said absorbent core assembly forming a body-facing side disposed confronting the perineum region of the person, whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself.

9. The undergarment of claim 8, wherein said absorbent core assembly additionally comprises an intermediate wicking layer disposed between said first and said section.

10. The undergarment of claim 9, wherein said wicking layer comprises an airlaid material.

11. The undergarment of claim 8, wherein said core comprises a fluid acquisition layer disposed over said first section of said core.

12. The undergarment of claim 8, wherein said first section of said core has a predetermined width and length, wherein said second section of said core has a predetermined width and length, and wherein said core comprises an intermediate nonwoven fluid transfer layer having a predetermined width which is less than the predetermined width of said first and second sections, said intermediate nonwoven fluid transfer layer being located between said first and second sections to facilitate the fluid transfer between said first and second sections.

13. The undergarment of claim 8, wherein said first section comprises a first layer of porous material and a second layer of porous material, each of said first and second layers being configured to permit the migration of a liquid therethrough and being quilted by fixedly secured securement lines to form a plurality of first pockets in said first layer and a plurality of first pockets in said second layer, with each of said first pockets being partially filled with a free, slow acting but high absorption capacity SAP.

14. A disposable absorbent undergarment configured to be worn by a person, said undergarment comprising:

an absorbent core assembly having a predetermined width and being configured for absorbing fluid from the person, said absorbent core assembly comprising a first section and a second section, said first section being formed of at least one layer of porous material configured to permit the migration of liquid therethrough, said at least one layer of porous material of said first section being quilted to form a plurality of first pockets, each of said first pockets being partially filled with a free, slow acting but high absorption capacity SAP, said second section being located below said first section and having a predetermined width and length, said second section being formed of a layer of porous material configured to permit the migration of liquid therethrough, said porous material of said second section being quilted to form a plurality of second pockets, each of said second pockets being partially filled with a free, fast acting but lower absorption capacity SAP, wherein the volume of SAP in at least some of said first pockets is within the range of approximately 25 to 35 percent of the volume of said first pockets, and wherein the volume of SAP in at least some of said second pockets is within the range of approximately 20 to 30 percent of the volume of said second pockets, said first section of said absorbent core assembly and said second section of said absorbent core assembly being in fluid communication with each other with said first section of said absorbent core assembly forming a body-facing side disposed confronting the perineum region of the person, whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself; and a chassis comprising a sheet of a cloth-like, non-woven, breathable material, said sheet having an inner surface, a front section, a back section, and an crotch section located between said front section and said back section, said front section including a top front edge, a pair of front side edges, and a plurality of elastic threads extending parallel to said top front edge and to each other from one of said pair of front side edges to the other of said pair of front side edges, said back section including a top back edge, a pair of back side edges, and a plurality of elastic threads extending parallel to said top back edge and to each other from one of said pair of back side edges to the other of said pair of back side edges, said crotch section comprising a pair of central side edges and a plurality of elastic threads extending parallel to said front top edge, to said back top edge, and to each other from one of said pair of central side edges to the other of said pair of central side edges, respective ones of said front side edges being secured to respective ones of said back side edges, each of said pair of central side sections comprising an ergonomically shaped recess forming a respective leg opening for the person, said recesses being spaced apart from each other by a distance which is greater than said predetermined width of said absorbent core assembly, said absorbent core assembly being secured on said inner surface of said chassis at said crotch section between said respective leg openings with plural ones of said plurality of elastic threads of said crotch section at said absorbent core assembly being cut into separated segments at the location of said core so as not to tend to collapse or buckle said core when said garment is worn by the person.

15. An absorbent core for an absorbent garment to be worn by a person, said core comprising:
a first section formed of at least a first layer and a second layer, each of said first and second layers being formed of a porous material configured to permit the migration of liquid therethrough and being quilted by fixedly secured securement lines to form a plurality of first pockets in said first layer and a plurality of first pockets in said second layer, each of said first pockets partially filled with a free, slow acting but high absorption capacity SAP, wherein the volume of SAP in at least some of said first pockets of said first layer is within the range of approximately 25 to 35 percent of the volume of said first pockets of said first layer, and wherein the volume of SAP in at least some of said first pockets of said second layer is within the range of approximately 80-120 percent of the volume or amount of SAP in said first pocket of said first layer and 25 to 35 percent of the volume or capacity of said first pockets of said second layer, said first section forming a body-facing side disposed confronting the perineum region of the person; and
a second section located below said first section and being in fluid communication with said first section, said second section having a predetermined width and length, said second section being formed of a layer of porous material of configured to permit the migration of a liquid therethrough, said layer of said second section being quilted to form a plurality of second pockets, each of said second pockets being partially filled with a free, fast acting but lower absorption capacity SAP, wherein the volume of SAP in at least some of said second pockets is within the range of approximately 20 to 30 percent of the volume of said second pockets, said core being configured whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself.

16. The absorbent core of claim 15 additionally comprising a fluid transfer or wicking layer disposed between said first section and said second section.

17. The absorbent core of claim 16, wherein said first section comprises a third layer formed of a porous material configured to permit the migration of liquid therethrough and being quilted by fixedly secured securement lines to form a plurality of first pockets in said third layer, and wherein the volume of SAP in at least some of said first pockets of said third layer is within the range of approximately 80 to 120 percent of the volume or amount of SAP in said first pockets of said first layer and 25 to 35 percent of the volume or capacity of said first pockets of said third layer.

18. An absorbent core for an absorbent garment to be worn by a person, said core comprising:
a first section formed of at least a first layer and a second layer, each of said first and second layers being formed of a porous material configured to permit the migration of liquid therethrough and being quilted by fixedly secured securement lines to form a plurality of first pockets in said first layer and a plurality of first pockets in said second layer, each of said first pockets partially filled with a free, slow acting but high absorption capacity SAP, wherein the SAP in said first section has a vortex time in the range of approximately 30 to 90 seconds, said first section forming a body-facing side disposed confronting the perineum region of the person; and
a second section located below said first section and being in fluid communication with said first section, said second section having a predetermined width and length, said second section being formed of a layer of porous material of configured to permit the migration of a liquid therethrough, said layer of said second section being quilted to form a plurality of second pockets, each of said second pockets being partially filled with a free, fast acting but lower absorption capacity SAP, wherein the volume of SAP in said second pockets is less than the volume of SAP in said first pockets and wherein the SAP in said second section has a vortex time of in the range of approximately 3 to 10 seconds, said core being configured whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself.

19. The absorbent core of claim 18, wherein the ratio of vortex time of said slow acting SAP to said fast acting SAP is within the range of approximately 6:1 to 3:1.

20. An absorbent core for an absorbent garment to be worn by a person, said core comprising:
a first section formed of at least a first layer, a second layer, and a third layer, each of said first and second layers being formed of a porous material configured to permit the migration of liquid therethrough and being quilted by fixedly secured securement lines to form a plurality of first pockets in said first layer and a plurality of first pockets in said second layer, wherein said third layer is formed of a porous material configured to permit the migration of liquid therethrough and being quilted by fixedly secured securement lines to form a plurality of first pockets in said third layer, with each of said first pockets of said first, second and third layers being partially filled with a free, slow acting but high absorption capacity SAP, wherein the SAP in said first section has a vortex time in the range of approximately 30 to 90 seconds, said first section forming a body-facing side disposed confronting the perineum region of the person; and
a second section located below said first section and being in fluid communication with said first section, said second section having a predetermined width and length, said second section being formed of a layer of porous material of configured to permit the migration of a liquid therethrough, said layer of said second section being quilted to form a plurality of second pockets, each of said second pockets being partially filled with a free, fast acting but lower absorption capacity SAP, wherein the SAP in said second section has a vortex time of in the range of approximately 3 to 10 seconds, said core being configured whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself.

21. An absorbent core for an absorbent garment to be worn by a person, said core having a longitudinal axis and comprising:
a first section formed of at least one layer of a porous material configured to permit the migration of liquid therethrough and being quilted by fixedly secured securement lines to form a plurality of first pockets in said at least one layer, each of said first pockets being partially filled with a free, slow acting but high absorption capacity SAP, each of said first pockets having a first pair of diametrically opposed corners and a second pair of diametrically opposed corners, and wherein said first pockets are oriented so that said first pair of diametrically opposed corners extend parallel to said longitudinal axis, said first section forming a body-facing side disposed confronting the perineum region of the person; and
a second section located below said first section and being in fluid communication with said first section, said second section being formed of a layer of porous material of configured to permit the migration of a liquid therethrough, said layer of said second section being quilted to form a plurality of second pockets, each of said second pockets being partially filled with a free, fast acting but lower absorption capacity SAP, each of said second pockets having a first pair of diametrically opposed corners and a second pair of diametrically opposed corners, and wherein said second pockets are oriented so that said first pair of diametrically opposed corners extend parallel to said longitudinal axis, with said second pockets being offset laterally or longitudinally with respect to said first pockets or with said second pockets being offset both laterally and longitudinally with respect to said first pockets, said core being configured whereupon fluid voided by the person flows in a tortuous path produced by said second pockets being offset from said first pockets, wherein said fluid is absorbed quickly and rapidly by said fast acting SAP, while said slow acting SAP desorbs or takes fluid away from said fast acting SAP as well as absorbing said fluid itself.

22. The absorbent core of claim 21 wherein said first section comprises a first layer and a second layer, each of said first and second layers being formed of a porous material configured to permit the migration of liquid therethrough and being quilted by fixedly secured securement lines to form a plurality of first pockets in said first layer and a plurality of first pockets in said second layer, each of said first pockets in each of said first and second layers being diamond shaped having a first pair of diametrically opposed corners and a second pair of diametrically opposed corners, and wherein said first pockets of said first and second layers are oriented so that said first pair of diametrically opposed corners extend parallel to said longitudinal axis.

23. The absorbent core of claim 21, wherein said diamond shaped pockets are square and in the range of approximately 1.5 cm. by 1.5 cm. to 3.0 cm. by 3.0 cm.

24. An absorbent core for an absorbent garment to be worn by a person, said absorbent core having a longitudinal axis and comprising:
a first absorbent section formed of a porous material having a first pair of longitudinally extending side edges, said first absorbent section comprising first and second layers configured to permit the migration of liquid therethrough, said first layer being disposed over said second layer, each of said first and second layers being quilted by fixedly secured securement lines to form a plurality of first pockets therein, said first pockets of said first layer being partially filled with a free, slow acting but high absorption capacity SAP, said first pockets of said second layer including outer first pockets located closely adjacent respective ones of said first pair of longitudinally extending side edges and inner first pockets located between said outer first pockets, each of said outer first pockets being partially filled with a free, slow acting but high absorption capacity SAP, each of said inner first pockets being partially filled with a free, slow acting but high absorption capacity SAP, with the volume of SAP in said outer first pockets being greater than the volume of SAP in said inner first pockets, said first section forming a body-facing side disposed confronting the perineum region of the person; and
a second absorbent section located below said first absorbent section and being in fluid communication with said first section, said second section being formed of a layer of porous material, said layer of said second section being configured to permit the migration of a liquid therethrough and being quilted to form a plurality of second pockets, said second pockets being partially filled with a free, fast acting but lower absorption capacity SAP, said core being configured whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself.

25. The absorbent core of claim 24, wherein said first section comprises another layer formed of a porous material and configured to permit the migration of liquid therethrough, said other layer being quilted by fixedly secured securement lines to form a plurality of first pockets therein, with each of said first pockets of said other layer being partially filled with a free, slow acting but high absorption capacity SAP.

26. The absorbent core of claim 24 wherein said outer first pockets make up approximately two thirds of the width of said first absorbent section.

27. The absorbent core of claim 24 additionally comprising a fluid transfer or wicking layer disposed between said first absorbent section and said second absorbent section.

28. An absorbent core for an absorbent garment to be worn by a person, said core having a longitudinal axis and comprising:
a first absorbent section having a width and being formed of first layer of a porous material and a second layer of porous material, said first layer being configured to permit the migration of liquid therethrough and being quilted by fixedly secured securement lines to form a plurality of first pockets in said first layer, said second layer being disposed under said first layer and configured to permit the migration of liquid therethrough, said second layer being quilted by fixedly secured securement lines to form a plurality of first pockets in said second layer, each of said first pockets of said first and second layers being partially filled with a free, slow acting but high absorption capacity SAP, at least some of said first pockets of said second layer also being partially filled with an odor absorbing material, said first layer of said first absorbent section forming a body-facing side disposed confronting the perineum region of the person;

a second absorbent section having a width and being located below said first absorbent section, said second absorbent section being in fluid communication with said first absorbent section, said second absorbent section being formed of a layer of porous material, said layer of said second absorbent section being configured to permit the migration of a liquid therethrough and being quilted to form a plurality of second pockets, said second pockets being partially filled with a free, fast acting but lower absorption capacity SAP, said absorbent core being configured whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself; and a fluid transfer or wicking layer disposed between said first absorbent section and said second absorbent section, said fluid transfer or wicking layer having a width that is less than the width of said first and second sections.

29. An absorbent core for an absorbent garment to be worn by a person, said core having a longitudinal axis and comprising:

a first absorbent section formed of first layer of a porous material, a second layer of porous material, and a third layer, said first layer being configured to permit the migration of liquid therethrough and being quilted by fixedly secured securement lines to form a plurality of first pockets in said at first layer, said second layer being disposed under said first layer and configured to permit the migration of liquid therethrough, said second layer being quilted by fixedly secured securement lines to form a plurality of first pockets in said second layer, each of said first pockets of said first and second layers being partially filled with a free, slow acting but high absorption capacity SAP, at least some of said first pockets of said second layer also being partially filled with an odor absorbing material, said first layer of said first section forming a body-facing side disposed confronting the perineum region of the person, wherein said first section comprises a third layer formed of a porous material and configured to permit the migration of liquid therethrough, said third layer being quilted by fixedly secured securement lines to form a plurality of first pockets therein, with each of said first pockets of said third layer being partially filled with a free, slow acting but high absorption capacity SAP; and a second absorbent section located below said first absorbent section and being in fluid communication with said first section, said second section being formed of a layer of porous material, said layer of said second section being configured to permit the migration of a liquid therethrough and being quilted to form a plurality of second pockets, said second pockets being partially filled with a free, fast acting but lower absorption capacity SAP said core being configured whereupon fluid voided by the person flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself.

\* \* \* \* \*